(12) United States Patent
Bar-Sagi et al.

(10) Patent No.: US 9,901,079 B2
(45) Date of Patent: Feb. 27, 2018

(54) INHIBITION OF ONCOGENIC KRAS-INDUCED GM-CSF PRODUCTION AND FUNCTION

(75) Inventors: Dafna Bar-Sagi, New York, NY (US); Yuliya Pylayeva-Gupta, New York, NY (US); Kyoung Eun Lee, Philadelphia, PA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/239,503

(22) PCT Filed: Aug. 20, 2012

(86) PCT No.: PCT/US2012/051602
§ 371 (c)(1),
(2), (4) Date: May 28, 2014

(87) PCT Pub. No.: WO2013/026059
PCT Pub. Date: Feb. 21, 2013

(65) Prior Publication Data
US 2014/0298498 A1 Oct. 2, 2014

Related U.S. Application Data

(60) Provisional application No. 61/525,052, filed on Aug. 18, 2011.

(51) Int. Cl.
| | |
|---|---|
| *A61K 39/395* | (2006.01) |
| *C07K 16/00* | (2006.01) |
| *A01K 67/027* | (2006.01) |
| *A61K 31/713* | (2006.01) |
| *G01N 33/574* | (2006.01) |
| *C07K 16/24* | (2006.01) |
| *C07K 16/28* | (2006.01) |
| *C12Q 1/68* | (2018.01) |

(52) U.S. Cl.
CPC ........ *A01K 67/0271* (2013.01); *A61K 31/713* (2013.01); *C07K 16/243* (2013.01); *C07K 16/2815* (2013.01); *C12Q 1/6886* (2013.01); *G01N 33/574* (2013.01); *G01N 33/57438* (2013.01); *G01N 33/57484* (2013.01)

(58) Field of Classification Search
None
See application file for complete search history.

(56) References Cited

U.S. PATENT DOCUMENTS

| 5,475,087 A | 12/1995 | Seelig et al. | |
|---|---|---|---|
| 7,867,495 B2 * | 1/2011 | Steidl .................. | C07K 16/243 424/130.1 |
| 2009/0053213 A1 | 2/2009 | Steidl et al. | |
| 2009/0215861 A1 | 8/2009 | Renzi et al. | |
| 2010/0272730 A1 | 10/2010 | Sass et al. | |
| 2011/0104172 A1 | 5/2011 | Plater-Zyberk | |

OTHER PUBLICATIONS

Tseng et al. J Immunotherapy 1997;20:334-42.*
Lo et al. Curr Cancer Drug Targets Dec. 2012;10:840-8.*
Jaffee et al. Hum Gene Ther 1998;9:1951-71.*
Lutz et al. Ann Surg. 2011;253:328-335.*
Le et al. J Immunother 2013;36:382-9.*
Germolec et al. Mutation Res 1997;386:209-18.*
Samuel et al. PloS One Feb. 2011;6:e17143.*
Bouabdallah et al. Leukemia & Lymphoma 1998;30:539-49.*
Rockova et al. Blood 2011;118:1069-76.*
MorphoSys datasheet, MOR103 antibody (Apr. 2007).*
Varshosaz et al. World J Gastroenterol 2015;21:12022-41.*
Ragnhammer et al. Blood 1994;84:4078-87.*
Sergeeva et al. Leukemia 2008;22:783-90.*
Jaffee et al. Cancer J Sci Am 1998;4:194-203.*
Dotson et al. Immunother 2011;3:517-37.*
Perkins et al. Brain Res Mol Brain Res 2003;111:42-51.*
Serafini et al. Semin Cancer Biol 2006;16:53-65.*
Pylayeva-Gupta, "Immune Response Modulation in KRas-Induced Pancreatic Neoplasia," New York University iCubed Retreat (Jun. 20, 2011).
Pylayeva-Gupta, "Immune Response Modulation in KRas-Induced Pancreatic Neoplasia," Cold Spring Harbor Laboratories Meeting: Mechanisms and Models of Cancer (Aug. 19, 2010).
Pylayeva-Gupta et al., "Role of KRas Activation in Modulating the Immune Response During Pancreatic Cancer Development," Poster Presentation, Cancer Research Institute Annual International Cancer Immunotherapy Symposia Series (Oct. 6, 2010).
Pylayeva-Gupta et al., "Role of KRas Activation in Modulating the Immune Response During Pancreatic Cancer Development," Poster Presentation, American Pancreatic Association Meeting (Nov. 4, 2010).
Lee et al., "Oncogenic KRas Suppresses Inflammation-Associated Senescence of Pancreatic Ductal Cells," Cancer Cell 18:448-458 (2010).
Serafini et al., "Phosphodiesterase-5 Inhibition Augments Endogenous Antitumor Immunity by Reducing Myeloid-Derived Suppressor Cell Function," J. Exp. Med. 203(12):2691-2702 (2006).
Cox et al., "Silencing the Killers: Paracrine Immune Suppression in Pancreatic Cancer," Cancer Cell 21:715-716 (2012).
Pylayeva-Gupta et al., "Oncogenic Kras-Induced GM-CSF Production Promotes the Development of Pancreatic Neoplasia," Cancer Cell 21:836-847 (2012) .
Dolcetti et al., "Hierarchy of Immunosuppressive Strength Among Myeloid-Derived Suppressor Cell Subsets is Determined by GM-CSF," Eur. J. Immunol. 40:22-35 (2010).
Marigo et al., "Tumor-Induced Tolerance and Immune Suppression Depend on the C/EBPβ Transcription Factor," Immunity 32:790-802 (2010).
Ko et al., "Direct and Differential Suppression of Myeloid-Derived Suppressor Cell Subsets by Sunitinib is Compartmentally Constrained," Cancer Res. 70(9):3526-3536 (2010).
Parmiani et al., "Opposite Immune Functions of GM-CSF Administered as Vaccine Adjuvant in Cancer Patients," Annals of Oncology 18:226-232 (2007).
Clark et al., "Dynamics of the Immune Reaction to Pancreatic Cancer from Inception to Invasion," Cancer Res. 67(19):9518-9527 (2007).

(Continued)

*Primary Examiner* — Janice Li
(74) *Attorney, Agent, or Firm* — LeClairRyan, a Professional Corporation

(57) ABSTRACT

The present invention is directed to methods of inhibiting tumor growth in a subject. The present invention is further directed to methods of diagnosing cancer in a subject and identifying a suitable course of treatment for the subject based on the diagnosis. The present invention is also directed to an orthotopic animal model of pancreatic cancer.

7 Claims, 15 Drawing Sheets

(56) References Cited

OTHER PUBLICATIONS

Mroczko et al., "Hematopoietic Cytokines in the Sera of Patients with Pancreatic Cancer," Clin Chem Lab Med 43(2):146-150 (2005).

Morse et al., "Countering Tumor-Induced Immunosuppression During Immunotherapy for Pancreatic Cancer," Expert Opin. Biol. Ther. 9(3):331-339 (2009).

Leishman et al., "Emerging Small Molecule and Biological Therapeutic Approaches for the Treatment of Autoimmunity," Expert Opin. Investig. Drugs 20(1):23-39 (2011).

Monfardini et al., "Rational Design of Granulocyte-Macrophage Colony-Stimulating Factor Antagonist Peptides," The Journal of Biological Chemistry 271(6):2966-2971 (1996).

International search report and written opinion for corresponding application No. PCT/US2012/051602, filed Aug. 20, 2012 (dated Jan. 23, 2013) (13 pages).

Bronte et al., "Unopposed Production of Granulocyte-Macrophage Colony-Stimulating Factor by Tumors Inhibits CD8+ T Cell Responses by Dysregulating Antigen-Presenting Cell Maturation," J. Immunol. 162:5728-5737 (1999).

Condamine et al., "Molecular Mechanisms Regulating Myeloid-Derived Suppressor Cell Differentiation and Function," Trends Immunol. 32(1):19-25 (2011).

Morales et al., "GM-CSF is One of the Main Breast Tumor-Derived Soluble Factors Involved in the Differentiation of CD11b-Gr1-Bone Marrow Progenitor Cells Into Myeloid-Derived Suppressor Cells," Breast Cancer Res. Treat. 123(1)39-49 (2010).

Rosenberg et al., "Myeloid-Derived Suppressor Cells: Linking Inflammation and Cancer," J. Immunol. 182:4499-4506 (2009).

Steube et al., "Secretion of Functional Hematopoietic Growth Factors by Human Carcinoma Cell Lines," Int. J. Cancer 78:120-124 (1998).

Qiu and Su, "Development of Orthotopic Pancreatic Tumor Mouse Models," Methods Mol. Biol. 980:215-223 (2013).

Tseng et al., "Development of an Orthotopic Model of Invasive Pancreatic Cancer in an Immunocompetent Murine Host," Clin. Cancer Res. 16(14):3684-3695 (2010).

Hingorani et al., "Preinvasive and Invasive Ductal Pancreatic Cancer and its Early Detection in the Mouse," Cancer Cell 4:437-450 (2003).

Bayne et al., "Tumor-derived Granulocyte-Macrophage Colony-stimulating Factor Regulates Myeloid Inflammation and T Cell Immunity in Pancreatic Cancer," Cancer Cell 21:822-835 (2012).

* cited by examiner

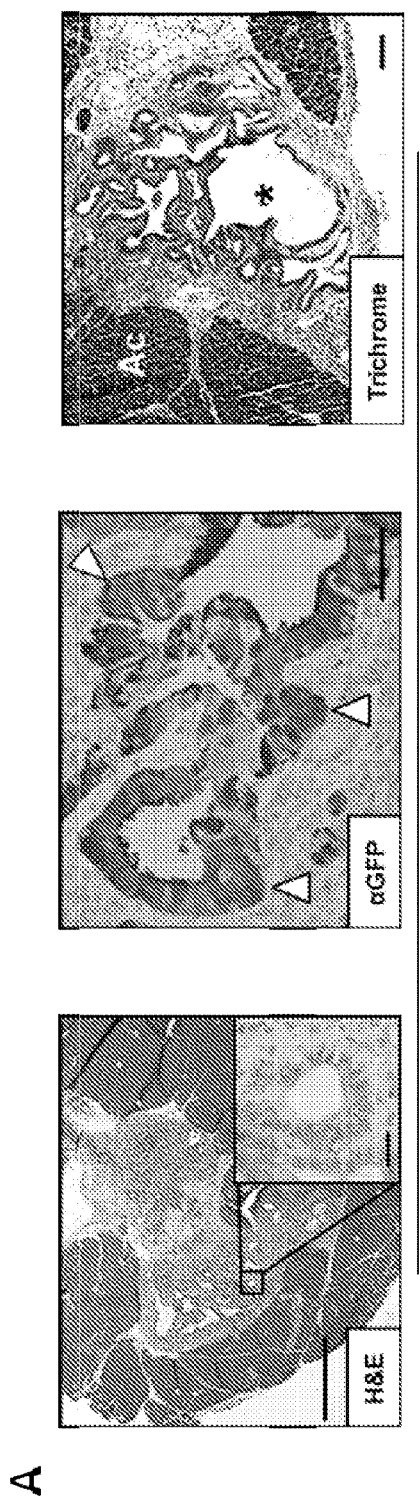
Figures 1A-1C

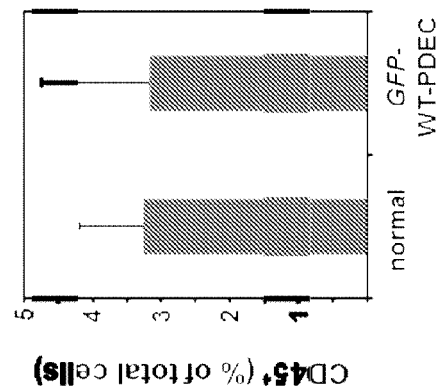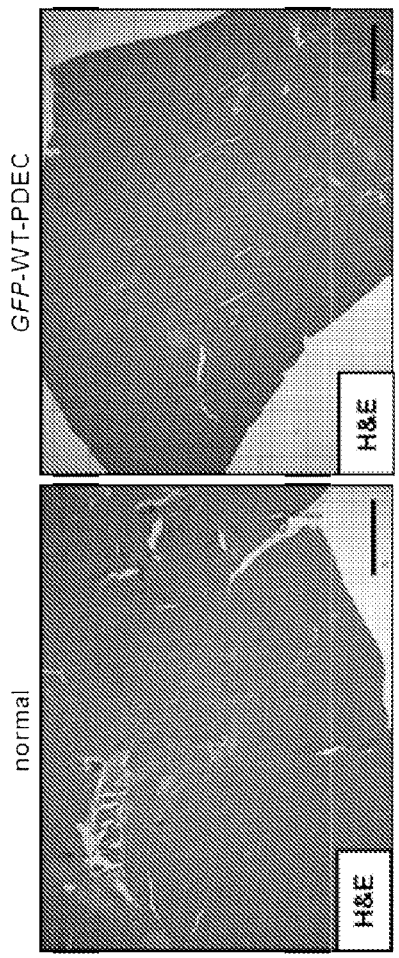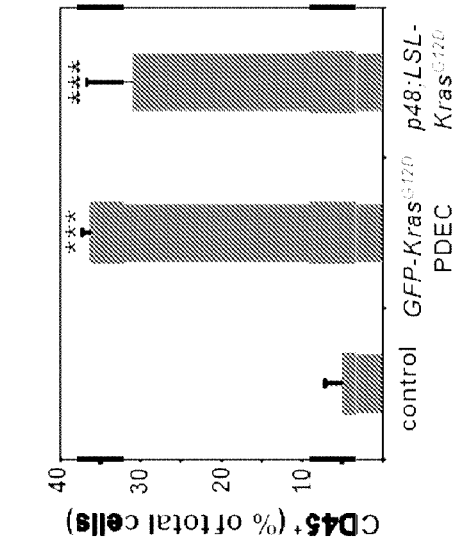
Figures 2A-2B

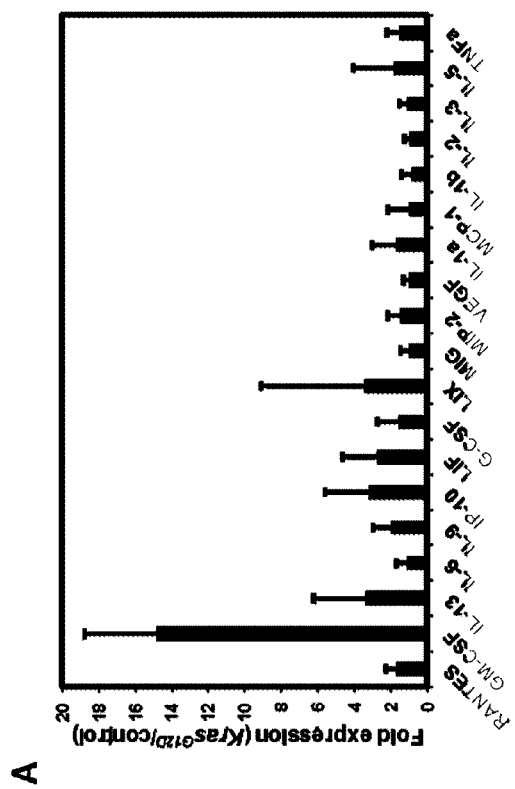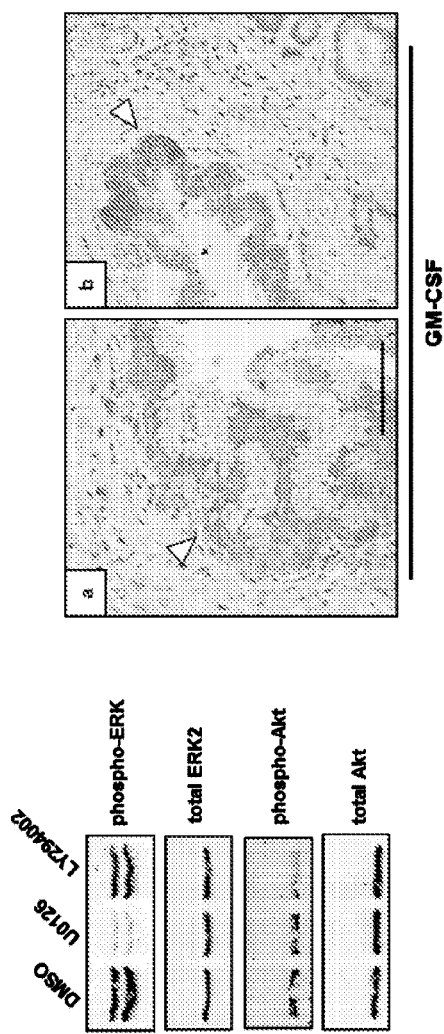
Figures 4A-4C

INHIBITION OF ONCOGENIC KRAS-INDUCED GM-CSF PRODUCTION AND FUNCTION

This application is a national stage application under 35 U.S.C. § 371 of PCT Application No. PCT/US2012/051602, filed Aug. 20, 2012, which claims the priority benefit of U.S. Provisional Patent Application Ser. No. 61/525,052, filed Aug. 18, 2011, which is hereby incorporated by reference in its entirety.

This invention was made with government support under grant number CA055360 awarded by the National Institutes of Health. The government has certain rights in this invention.

FIELD OF THE INVENTION

The present invention is directed to methods of diagnosing, preventing, and treating cancer in a subject. The present invention also relates to an orthotopic animal model of pancreatic cancer.

BACKGROUND OF THE INVENTION

Oncogenic mutations in Ras-encoding genes are found in approximately 30% of all tumors and are most prevalent in carcinomas of the pancreas, colon, lung, and bladder. These mutations have profound effects on proliferation, cell survival, and tumor invasion. Ras orchestrates these events by activating downstream effector pathways that regulate actin reorganization and gene expression.

Pancreatic ductal adenocarcinoma (PDA) is a highly aggressive malignancy with a dismal long term prognosis. The disease exhibits a median survival of less than 6 months and a 5-year survival rate of 3-5% (Maitra et al., "Pancreatic Cancer," *Annu. Rev. Pathol.* 3:157-188 (2008) and Shi et al., "Sensitive and Quantitative Detection of KRAS2 Gene Mutations in Pancreatic Duct Juice Differentiates Patients with Pancreatic Cancer from Chronic Pancreatitis, Potential for Early Detection," *Cancer Biol. Ther.* 7:353-360 (2008)). PDA evolves through a series of histopathological changes, referred to as pancreatic intraepithelial neoplasia (PanIN), accompanied by a recurrent pattern of genetic lesions the earliest and most ubiquitous of which is oncogenic activation of Kras (Maitra et al., "Pancreatic Cancer," *Annu. Rev. Pathol.* 3:157-188 (2008) and Shi et al., "Sensitive and Quantitative Detection of KRAS2 Gene Mutations in Pancreatic Duct Juice Differentiates Patients with Pancreatic Cancer from Chronic Pancreatitis, Potential for Early Detection," *Cancer Biol. Ther.* 7:353-360 (2008)). The essential role of oncogenic Kras in the pathogenesis of PDA is indicated by several genetically engineered mouse models where conditional expression of the mutated allele of Kras in the pancreas is necessary and/or sufficient to drive disease progression from the early preinvasive stage to a malignant stage (Hingorani et al., "Preinvasive and invasive ductal pancreatic cancer and its early detection in the mouse," *Cancer Cell* 4:437-450 (2003); Hingorani et al., "Trp53R172H And KrasG12D Cooperate to Promote Chromosomal Instability and Widely Metastatic Pancreatic Ductal Adenocarcinoma in Mice," *Cancer Cell* 7:469-483 (2005) and Seidler et al., "A Cre-Loxp-Based Mouse Model for Conditional Somatic Gene Expression and Knockdown In Vivo by Using Avian Retroviral Vectors," *Proc. Natl. Acad. Sci. U.S.A.* 105:10137-10142 (2008)). Though the mechanisms by which oncogenic Kras contributes to the genesis and progression of PDA have not been fully elucidated, the proliferative and survival advantage conferred on epithelial cells by the expression of oncogenic Kras has been clearly implicated (Lee et al., "Oncogenic Kras Suppresses Inflammation-Associated Senescence of Pancreatic Ductal Cells," *Cancer Cell* 18:448-458 (2010)).

In addition to the well-documented molecular and histological alterations exhibited by the tumor cells themselves as well as their pre-neoplastic precursors, a hallmark of PDA is an extensive stromal remodeling, the most prominent features of which are the recruitment of inflammatory and mesenchymal cells and fibrotic replacement of the pancreatic parenchyma (Chu et al., "Stromal Biology of Pancreatic Cancer," *J. Cell Biochem.* 101:887-907 (2007) and Maitra et al., "Pancreatic Cancer," *Annu. Rev. Pathol.* 3:157-188 (2008)). Strikingly, histological assessment of pancreata of afflicted human patients or mice engineered to express oncogenic Kras in the epithelial compartment of the pancreas reveal that even early stages of PanIN are associated with a stromal reaction which is characterized by a robust desmoplastic response and recruitment of immune cells (Chu et al., "Stromal Biology of Pancreatic Cancer," *J. Cell Biochem.* 101:887-907 (2007) and Clark et al., "Dynamics of the Immune Reaction to Pancreatic Cancer From Inception to Invasion," *Cancer Res.* 67:9518-9527 (2007)). The precise role played by the PanIN-associated stroma in PDA development has not been established. Based on the composition of the immune infiltrates surrounding the PanINs it has been proposed that the stromal constituents around PanINs form an inflammatory and immune suppressive environment thereby allowing the precursor lesion to escape immune surveillance (Clark et al., "Immunosurveillance of Pancreatic Adenocarcinoma: Insights From Genetically Engineered Mouse Models Of Cancer," *Cancer Lett.* 279: 1-7 (2009)). Consistent with this idea, studies in both humans and mice have demonstrated a dampened adaptive immune response accompanying the formation of oncogenic Ras-driven cancers (Clark et al., "Immunosurveillance of Pancreatic Adenocarcinoma: Insights From Genetically Engineered Mouse Models Of Cancer," *Cancer Lett.* 279: 1-7 (2009); DuPage et al., "Endogenous T Cell Responses to Antigens Expressed in Lung Adenocarcinomas Delay Malignant Tumor Progression," *Cancer Cell* 19:72-85 (2011); Fossum et al., "CD8+ T Cells From a Patient with Colon Carcinoma, Specific for a Mutant P21-Ras-Derived Peptide (Gly13-->Asp), are Cytotoxic Towards a Carcinoma Cell Line Harbouring the Same Mutation," *Cancer Immunol. Immunother.* 40:165-172 (1995); Gjertsen et al., "Mutated Ras Peptides as Vaccines in Immunotherapy of Cancer," *Vox Sang* 74(Suppl 2):489-495 (1998); Kubuschok et al., "Naturally Occurring T-Cell Response Against Mutated P21 Ras Oncoprotein in Pancreatic Cancer," *Clin. Cancer Res.* 12:1365-1372 (2006); Qin et al., "CD4+T-Cell Immunity to Mutated Ras Protein in Pancreatic and Colon Cancer Patients," *Cancer Res.* 55:2984-2987 (1995); and Weijzen et al., "Modulation of The Immune Response and Tumor Growth by Activated Ras," *Leukemia* 13:502-513 (1999)). Moreover, there is growing evidence that targeting the tumor immune microenvironment may provide an effective therapeutic strategy (Quezada et al., "Shifting the Equilibrium in Cancer Immunoediting: From Tumor Tolerance to Eradication," *Immunol. Rev.* 241:104-118 (2011)).

The present invention is directed to overcoming these and other deficiencies in the art.

SUMMARY OF THE INVENTION

A first aspect of the present invention is directed to a method of inhibiting tumor growth in a subject. This method involves selecting a subject having a tumor, where the tumor cells have an activated oncogene and administering to the selected subject an agent that inhibits granulocyte macrophage colony stimulating factor (GM-CSF) and/or an agent that inhibits myeloid derived suppressor cell (MDSC) activity under conditions effective to inhibit tumor growth in the subject.

Another aspect of the present invention relates to a method of preventing tumor formation in a subject. This method involves selecting a subject susceptible to tumor formation and administering to the selected subject an agent that inhibits GM-CSF and/or MDSC activity under conditions effective to prevent tumor formation in the subject.

Another aspect of the present invention is directed to a method of diagnosing a subject as having or not having cancer. This method involves obtaining a sample from a subject and measuring GM-CSF levels and/or MDSC levels in the sample. The measured GM-CSF and/or MDSC levels in the sample are compared to GM-CSF and/or MDSC levels, respectively, in a reference sample, and the subject is diagnosed as having or not having cancer based on this comparison.

Another aspect of the present invention is directed to a method of treating a subject having cancer. This method involves measuring GM-CSF levels and/or MDSC levels in a cancerous sample from the subject and comparing the measured GM-CSF and/or MDSC levels in the sample to GM-CSF and/or MDSC levels, respectively, in a reference sample. This method further involves selecting a treatment for the subject having cancer based on the comparison and administering the selected treatment to the subject.

Another aspect of the invention relates to a method of producing an orthotopic non-human mammal model of pancreatic cancer. This method involves introducing oncogenic pancreatic duct epithelial cells into pancreatic tissue of a recipient non-human mammal under conditions effective for the formation of pancreatic cancer, thereby producing an orthotopic non-human mammal model of pancreatic cancer.

Another aspect of the present invention is directed to an orthotopic non-human mammal model of pancreatic ductal adenocarcinoma that comprises pancreas-specific mutational activation of Kras.

Pancreatic ductal adenocarcinoma (PDA) is a highly aggressive malignancy currently ranked as the fourth-leading cause of cancer-related deaths in the United States. PDA development is accompanied by pronounced changes in stromal responses and immune surveillance programs. However, the mechanisms that contribute to these changes have not been clearly defined. As demonstrated herein, mutational activation of Kras in pancreatic ductal cells triggers the production of GM-CSF, which, in turn, promotes the expansion of immunosuppressive $Gr1^+CD11b^+$ myeloid cells, leading to the evasion of $CD8^+$ T cell-driven antitumor immunity. Moreover, disrupting PDEC GM-CSF secretion or neutralization GM-CSF activity inhibits pancreatic tumor growth and maintenance. These findings not only implicate oncogenic Kras in restraining the antitumor immune response, but also provide insights into critical barriers for designing effective immunotherapeutic strategies against pancreatic cancer.

BRIEF DESCRIPTION OF THE DRAWINGS

FIGS. 1A-1D show the generation of a robust immune response upon orthotopic implantation of $Kras^{G12D}$-Pancreatic ductal epithelial cells ("PDEC"). FIG. 1A shows histological tissue sections from orthotopic pancreatic grafts formed by GFP-Kras $^{G12D}$-PDEC at 4 weeks post-implantation that were stained with hematoxylin and eosin ("H&E"; scale bar=500 μm); anti-GFP antibody ("GFP"; scale bar=50 μm) and Trichrome blue ("Trichome"; scale bar=100 μm). White arrowheads indicate GFP-positive neoplastic pancreatic ducts; black asterisk indicates neoplastic ducts; Ac stands for acinar compartment. FIG. 1B shows immunofluorescence staining for CD45 and CK19 in pancreatic tissue sections from normal sham injected control and orthotopic GFP-Kras$^{G12D}$-PDEC animals (4 weeks post implantation). CK19 was used to identify ductal epithelia, CD45 was used to identify immune cells, and nuclei were counterstained with DAPI. White asterisk indicates pancreatic ductal structures (left panel) and grafted ductal structures (right panel). White arrowheads indicate $CD45^+$ cells. Scale bars=100 μm. The percentage of immune cell types in pancreata was determined by flow cytometry of the entire pancreatic tissue and quantitation of the results is shown in the graph of FIG. 1C (gray bars-Kras$^{G12D}$-PDEC at 8 weeks post implantation; black bars-LSL-Kras$^{G12D}$). After gating on the CD45 population, cells were analyzed for the presence of respective lineage markers (percent of each immune cell subtype out of total number of live cells sorted from the pancreas is shown). Error bars indicate SD (n=3-8 mice per group). FIG. 1D shows the flow cytometry analysis of pancreatic tissue for the presence of $Gr1^+CD11b^+$ myeloid and $Foxp3^+CD25^+$ T regulatory cells (Tregs). After gating on the CD45 population, cells were analyzed for the presence of $Gr1^+CD11b^+$ subpopulation (top, representative flow cytometry plots). The graph (top, right) shows the percentage $Gr1^+CD11$ cells out of total number of live cells sorted from the pancreas. After gating on $CD45^+CD3^+$ T cells, cells were gated on $CD4^+$ to examine intracellular Foxp3 versus surface CD25 staining (bottom, representative flow cytometry plot). The graph shows the percentage of Tregs out of total number of CD4+T cells. Error bars indicate SD; INS—insufficient number of cells for analysis, (n=4-8 mice per group). p value: *<0.05; **<0.01; NS—not significant.

FIGS. 2A-2D depict the overall abundance and subtype distribution of immune cells in pancreata containing Kras$^{G12D}$-PDEC grafts and pancreata from LSL-$^{KrasG12D}$; p48-Cre mice (LSL-$^{KrasG12D}$). FIG. 2A shows H&E staining of normal uninjected pancreas and pancreas grafted with GFP-wildtype (WT)-PDEC at 4 weeks post-implantation. Scale bar=500 μm. The graph to the right shows the percentage of CD45 immune cells in normal and orthotopic GFP-WT-PDEC (4 weeks post-implantation) pancreata that was determined by flow cytometry of the pancreatic tissue. Error bars indicate SD (n=3 mice per group). FIG. 2B is a graph showing the percentage of CD45 cells in the pancreata orthotopically injected with GFP-WT-PDECs (control, 8 weeks post-implantation) or GFP-Kras$^{G12D}$-PDEC (8 weeks post-implantation), or p48-Cre;LSL-Kras$^{G12D}$ pancreas (12 weeks old), as determined by fluorescence-activated cell sorting (FACS). Error bars indicate SD (n=5-7 mice per group). FIG. 2C shows representative flow cytometry plots (left) and quantification (graph, right) of the cells expressing Gr1 or CD11b markers in the splenic tissue from normal, orthotopically injected GFP-Kras$^{G12D}$ -PDEC at 4 weeks post-implantation or p48-Cre;LSL-Kras$^{G12D}$ (4 months old) animals. Numbers in the flow cytometry plots indicate percentages of $Gr1^-CD11b$ (gray bars) and $Gr1^+CD11b^+$ cells (black bars) among total cells sorted. Error bars indicate SD (n=3-8 mice per group). FIG. 2D show representative flow cytometry plots (left) and quantification (graph, right) of the cells expressing intracellular Foxp3 and surface CD25 in the splenic tissue from normal, orthotopically injected GFP-Kras$^{G12D}$-PDEC at 4 weeks post-implantation or p48-Cre;LSL-Kras$^{G12D}$ (4 months old) animals. Numbers in the flow cytometry plots indicate percentages of Foxp3$^+$CD25$^+$ cells among CD4$^+$ T cells. Error bars indicate SD (n=4-8 mice per group). p value: *<0.05; <0.01; *<0.001.

FIG. 3A is a bar graph showing levels of GM-CSF mRNA (black bar) and protein (gray bars) in GFP-Kras$^{G12D}$-PDEC assessed by quantitative RT-PCR and ELISA, respectively. Data are presented as an average fold induction over values from GFP-WT-PDEC or normal pancreata. Error bars indicate SD (n=3). FIG. 3B shows the normalized expression of GM-CSF mRNA in GFP-Kras$^{G12D}$-PDEC s (black bars) after 24 hour treatment with DMSO, MAPK inhibitor U0126 (2 µM), or PI3K inhibitor LY294002 (10 µM) that was analyzed by quantitative RT-PCR. Error bars indicate SD (n=3). FIG. 3C is a graph depicting the relative levels of GM-CSF protein in pancreata grafted with GFP-Kras$^{G12D}$-PDEC or pancreata from p48-Cre;LSL-Kras$^{G12D}$ mice. Data are presented as an average fold induction over values from normal pancreatic tissue. Error bars indicate SD (n=3). FIG. 3D are photomicrographs showing immunohistochemical staining for GM-CSF protein in representative samples of human pancreatic cancer containing PanIN lesions (i—normal duct from adjacent non-malignant tissue; ii-iii PanIN lesions; iv—invasive PDA). White arrowheads indicate pancreatic duct (i), PanIN (ii and iii), and PDA (iv). Scale bars=50 µm.

FIGS. 4A-4C show cytokine expression in Kras$^{G12D}$-PDECs. FIG. 4A is a graph showing protein expression levels detected by ELISA of the indicated cytokines in supernatants from GFP-Kras$^{G12D}$-PDEC. The expression data is presented as an average fold induction over values from supernatants of GFP-WT-PDEC (control). Five pairs of GFP-Kras$^{G12D}$- and GFP-WT-PDEC (10 cell lines total) were used in the analysis. The remaining cytokines in the Milliplex bead array kit were undetectable. Error bars indicate SD (n=3). FIG. 4B shows the Western blot analysis for the indicated antibodies that was performed on lysates from GFP-WT- and GFP-Kras$^{G12D}$-PDEC after 24 hour treatment with DMSO, MAPK inhibitor U0126 (20 µM), or PI3K inhibitor LY294002 (100 µM). FIG. 4C shows immunohistochemical staining for GM-CSF protein in samples of human pancreatic cancer and chronic pancreatitis. (a—PanIN-like lesion in the sample of chronic pancreatitis; b—PDA-associated PanIN lesion). White arrowheads indicate pancreatic lesion (a) and PanIN (b). Scale bar, 100 µm.

FIG. 5A shows the flow cytometry analysis of Lin$^{neg}$CD34$^+$ hematopoietic progenitor cells for the surface markers CD11b and Gr1 following co-culture with GM-CSF or GFP-Kras$^{G12D}$-PDEC with or without α-GM-CSF antibody (α-GM). Representative flow cytometry plots (left) and quantification graph (right) indicating the percentage of Gr1$^+$CD11b$^+$ cells out of the total number of live cells is shown. Error bars indicate SD (n=3). FIG. 5B is a graph showing the quantitation of BrdU$^+$CD3$^+$ T cells treated as indicated. T cells and Gr1$^+$CD11b$^+$ cells were co-cultured at 1:1 ratio. Error bars indicate SD (n=3). FIG. 5C is a graph showing representative quantification of BrdU$^+$CD3$^+$ T cells co-cultured with either Gr1$^-$CD11b$^+$ or Gr1$^+$CD11b$^+$ cells isolated from mouse pancreata 8 weeks after injection with GFP-Kras$^{G12D}$-PDECs. For proliferation assays, myeloid cells and T cells were cultured at ratios of 1:1, 1:5, or 1:10 respectively. T cells incubated in αCD3-coated wells and in the presence of aCD28 serve as control. Error bars indicate SD (n=3). FIG. 5D shows the expression of mouse GM-CSF in sera of either uninjected mice (control, n=4) or mice with GFP-Kras$^{G12D}$-PDEC grafts 8 weeks after implantation (n=5) measured using ELISA. Each symbol represents a mouse, and mean values for each group are represented by black lines. FIG. 5E is a graph showing the relative expression of GM-CSF mRNA (gray bars, left axis) and protein (black bars, right axis) in GFP-Kras$^{G12D}$-PDEC 4 days after infection with lentiviruses containing either scrambled shRNA (scr) or GM-CSF shRNAs (GM-sh1, GM-sh2) as assessed by quantitative RT-PCR and ELISA. Error bars indicate SD (n=3). FIG. 5F is an in vitro growth analysis curve of scr (circles) and GM-sh1 (squares) and GM-sh2 (triangles) GFP-Kras$^{G12D}$-PDEC that was assessed by MTT assay. Error bars indicate SD, (n=3). FIG. 5G are representative flow cytometry plots of pancreatic immune cells showing surface expression of Gr1 and CD11b markers at 4-weeks post-implantation of scr, GM-sh1, and GM-sh2 GFP-Kras$^{G12D}$-PDEC. After gating on the CD45 population, cells were analyzed for the presence of CD11b$^+$ and Gr1$^+$ populations. In FIG. 5H, quantification of the relative abundance of Gr1$^+$CD11b$^+$ and Gr1$^-$CD11b$^+$ cell populations is presented as a percentage change in CD45$^+$ single-positive Gr1$^-$CD11b$^+$ cells (black bars) and double positive Gr1$^+$CD11b$^+$ population (gray bars) relative to scr GFP-Kras$^{G12D}$-PDEC. Error bars indicate SD (n=6 mice per group). p value: <0.01; *<0.001

FIG. 6B shows immunohistochemical staining for GFP on pancreatic sections of scr- and GM-sh GFP-Kras$^{G12D}$-PDEC orthotopic grafts at 1 and 2 weeks post-implantation. Asterisks indicate engrafted area. Scale bar=100 µm. p value: *<0.05

FIG. 8A shows immunohistochemical staining (photomicrographs; left) and quantification (bar graph; right) of CD8 and cleaved caspase 3 expression on sections of scr- and GM-sh GFP-Kras$^{G12D}$-PDEC orthotopic grafts at 2 weeks post-implantation. CD8$^+$ or cleaved caspase3-positive cells within the boundaries of orthotopic grafts were counted per field of view (FOV) at 20× magnification. White arrowheads indicate CD8$^+$ cells; black arrowheads indicate caspase-3-positive cells. Scale bars=50 µm. Error bars indicate SD (n=4 mice per group, 4

FOV per mouse). FIG. 8B shows immunohistochemical staining for CD8 and B220 on consecutive sections of scr- and GM-sh GFP-Kras$^{G12D}$-PDEC orthotopic grafts at 4 weeks post-implantation (left). Numbers of CD8$^+$ cells were counted per FOV at 20× magnification as shown in the graph (right). Arrows indicate coaggregation of CD8$^+$ cells and B220$^+$ cells. Scale bar=100 μm. Error bars indicate SD (n=3 mice per group, 5 FOV per mouse). p value: ***<0.001.

FIG. 9A shows immunohistochemical staining and quantification of CD8$^+$ and cleaved caspase 3-positive cells on sections of scr- and GM-sh-GFP-Kras$^{G12D}$-PDEC orthotopic grafts at 1 week post-implantation. CD8$^+$ or cleaved caspase3-positive cells within the boundaries of orthotopic grafts were counted per FOV at 20× magnification. Scale bars, 100 μm. Error bars indicate SD (n=5 mice per group, 4 FOV per mouse). FIG. 9B shows H&E and anti-CD8 staining of the lesions formed by GFP-negative scr- and GM-sh-GFP-Kras$^{G12D}$-PDEC at 2 weeks post-implantation. CD8$^+$ cells within the boundaries of orthotopic grafts were counted per FOV at 20× magnification. Black asterisks indicate pancreatic neoplastic ducts; white arrowheads indicate CD8$^+$ cells. Scale bars, 100 μm. Error bars indicate SD (n=4 mice per group, 4 FOV per mouse). p value: ***<0.001; NS—not significant.

FIG. 10B shows the extent of colonization of the grafted areas by scr- or GM-sh GFP-Kras$^{G12D}$-PDECs in mock-depleted (IgG) or CD8-depleted animals at 2 weeks after implantation as analyzed by GFP immunohistochemistry. Scale bar, 100 mm. FIG. 10C is a graph depicting the quantification of the data from FIG. 10B, indicating the fraction of GFP$^+$ area per total area of the graft. Error bars indicate SD (n=4 mice per group, 5 FOV per mouse). ***p<0.001; NS, not significant.

DETAILED DESCRIPTION OF THE INVENTION

Figure 1D:
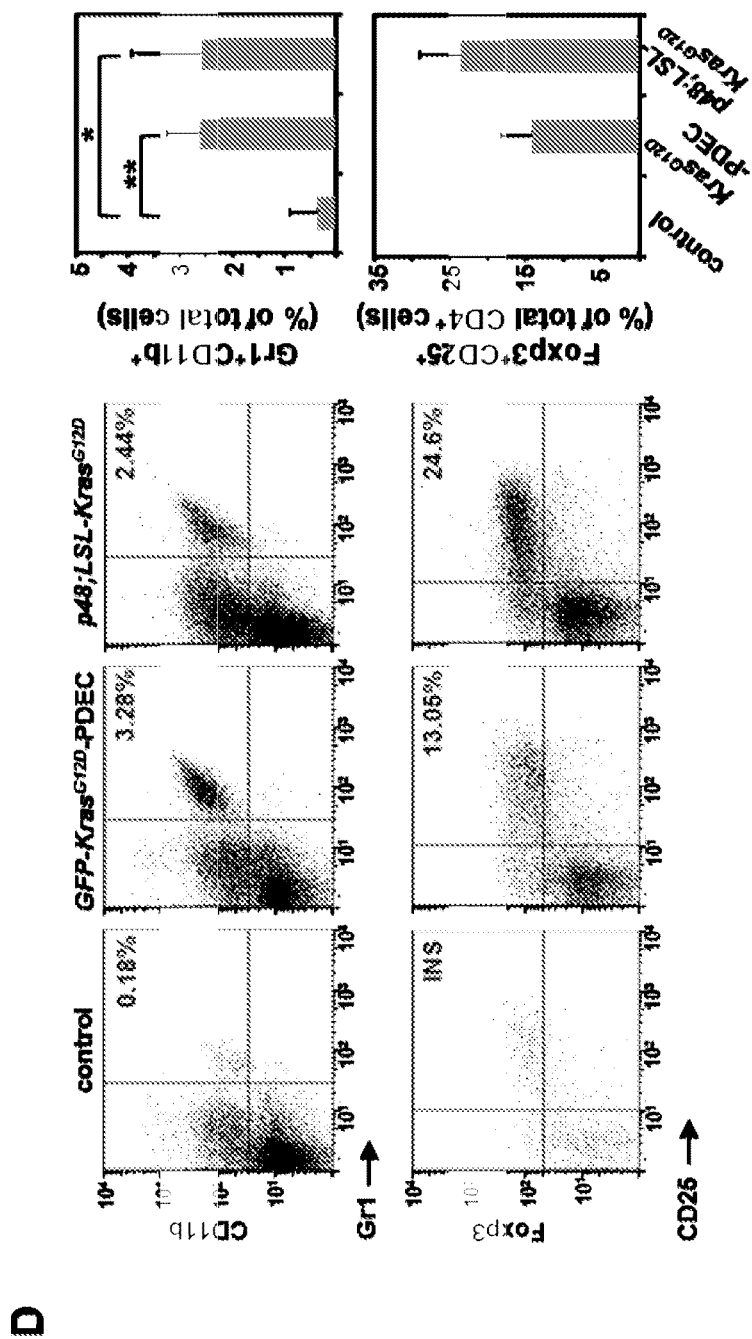

A first aspect of the present invention is directed to a method of inhibiting tumor growth in a subject. This method involves selecting a subject having a tumor, where the tumor cells have an activated oncogene and administering to the selected subject an agent that inhibits granulocyte macrophage colony stimulating factor (GM-CSF) and/or an agent that inhibits myeloid derived suppressor cell (MDSC) activity under conditions effective to inhibit tumor growth in the subject.

In accordance with this and all other aspects of the present invention, a "subject" or "patient" encompasses any animal, preferably, a mammal. Exemplary mammalian subjects include, without limitation, humans, non-human primates, dogs, cats, rodents (e.g., mouse, rat, guinea pig), horses, cattle and cows, sheep, and pigs. In a preferred embodiment of the present invention the subject is a human.

In accordance with this aspect of the invention, a subject having a tumor is selected prior to administration of a therapeutic agent, i.e., a GM-CSF inhibitor or an agent that inhibits MDSC activity. In one embodiment of the present invention the tumor is characterized by tumor cells having an activated oncogene. As used herein, "oncogene" is a gene that plays a normal role in the cell as a proto-oncogene, but has been altered by mutation and contributes to the growth of a tumor. Oncogenes are well known in the art and include, without limitation, Ras, c-Sis/PDGF-β, epidermal growth factor receptor (EGFR), platelet-derived growth factor receptor (PDGFR), vascular endothelial growth factor receptor (VEGF), HER2/neu, Src-family of oncogenes, Syk-ZAP-70 family of tyrosine kinases, BTK family of tyrosine kinases, Abl, Raf kinase, cyclin-dependent kinases, myc, Wnt, and Trk. In one embodiment of the present invention, the subject has a tumor expressing a Ras oncogene, e.g., a mutant HRas gene, mutant NRas gene, or a mutant KRas gene. In a preferred embodiment of the present invention, the subject has a tumor expressing a KRas oncogene. Tumors that may comprise an activated oncogene and are suitable for treatment in accordance with the methods of the present invention include, without limitation, pancreatic tumors, breast tumors, bladder tumors, melanoma, lung tumors, ovarian tumors, colorectal tumors, thyroid tumors, liver tumors, or leukemia. In a preferred embodiment of the present invention, the selected subject has a pancreatic tumor.

In another embodiment of the present invention, the subject has a tumor that is characterized by tumor cell overexpression of GM-CSF. "Overexpression of GM-CSF" as used herein refers to any level of GM-CSF production or secretion by a tumor cell that is higher than the level of GM-CSF production or secretion by a non-tumor cell of the same or similar origin. Tumors which may overexpress GM-CSF include any of the tumors described supra.

In yet another embodiment of the invention, the subject has a tumor that is characterized by tumor cell activation of ERK and or PI-3K.

Suitable therapeutic agents of the invention for this and other aspects of the present invention encompass agents that inhibit GM-CSF directly or inhibit its downstream activity or effectors. GM-CSF binds to a heterodimeric receptor comprised of GMRα and a common β subunit, βc. Key proteins involved in the GM-CSF pathway include JAK2, STAT5, SHP-2, RAS and Raf-1. The term "GM-CSF inhibitor" refers to any molecule which can block, suppress or reduce gene expression, protein production and processing, release, and/or biological activity of GM-CSF, its biological receptor, co-receptor, or co-ligand, or a defined polypeptide in the GM-CSF pathway. Defined polypeptides in the GM-CSF pathway are GMRα/β-c, JAK2, STAT5, SHP-2, RAS, Raf-1, Erk, and PI-3K.

Suitable therapeutic agents of the invention further include agents that inhibit MDSC activity either by inhibiting the differentiation of progenitor Gr-1$^-$CD11b$^-$ cells to Gr-1$^+$CD11b$^+$ MDSCs, inhibiting MDSC recruitment to the tumor microenvironment, or inhibiting MDSC immunosuppressive activity. Exemplary inhibitory agents of GM-CSF and MDSC are described below and include nucleic acid inhibitor molecules, protein or peptide inhibitors, antibodies, and small molecule inhibitors.

In one embodiment of the invention, the GM-CSF inhibitor is a nucleic acid inhibitor. Exemplary nucleic acid inhibitors of GM-CSF include antisense RNAs or RNAi, such as short interfering RNAs (siRNA), short hairpin RNAs (shRNA), and microRNAs.

The use of antisense methods to inhibit the in vivo translation of genes and subsequent protein expression is well known in the art (see e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," *Scientific Am.* 262:40-46 (1990), which is hereby incorporated by reference in its entirety). The antisense nucleic acid molecule hybridizes to its corresponding target nucleic acid molecule, such as GM-CSF mRNA, to form a double-stranded molecule, which interferes with translation of the mRNA, as the cell will not translate a double-stranded mRNA. The nucleotide sequence of human GM-CSF mRNA, which can be used for designing antisense and other nucleic acid inhibitory molecules, is known in the art, see NCBI Reference Sequence No. NM_000758, which is hereby incorporated by reference in its entirety, and is provided below as SEQ ID NO:1.

```
  1    acacagagag aaaggctaaa gttctctgga ggatgtggct
       gcagagcctg ctgctcttgg 61    gcactgtggc ctgcagcatc tctgcacccg cccgctcgcc
       cagccccagc acgcagccct 121    gggagcatgt gaatgccatc caggaggccc ggcgtctcct
       gaacctgagt agagacactg 181    ctgctgagat gaatgaaaca gtagaagtca tctcagaaat
       gtttgacctc caggagccga 241    cctgcctaca gacccgcctg gagctgtaca agcagggcct
       gcggggcagc ctcaccaagc 301    tcaagggccc cttgaccatg atggccagcc actacaagca
       gcactgccct ccaacccgg 361    aaacttcctg tgcaacccag attatcacct ttgaaagttt
       caaagagaac ctgaaggact 421    ttctgcttgt catcccttt gactgctggg agccagtcca
       ggagtgagac cggccagatg 481    aggctggcca agccggggag ctgctctctc atgaaacaag
       agctagaaac tcaggatggt 541    catcttggag ggaccaaggg gtgggccaca gccatggtgg
       gagtggcctg gacctgccct 601    gggccacact gaccctgata caggcatggc agaagaatgg
       gaatatttta tactgacaga 661    aatcagtaat atttatatat ttatattttt aaaatattta
       tttatttatt tatttaagtt 721    catattccat atttattcaa gatgttttac cgtaataatt
       attattaaaa atatgcttct 781    a (SEQ ID NO: 1)
```

Antisense nucleic acid molecules used in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the GM-CSF nucleotide sequence (SEQ ID NO:1). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. siRNA molecules that effectively interfere with GM-CSF expression have been developed (e.g., OriGene and Santa Cruz Biotechnology, Inc.) and are suitable for use in the present invention. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively interfere with GM-CSF expression are described herein and are suitable for use in the methods of the present invention.

Nucleic acid aptamers that specifically bind to GM-CSF are also useful in the methods of the present invention. Nucleic acid aptamers are single-stranded or partially single-stranded, nucleotide sequences capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

Therapeutic agents that inhibit GM-CSF signaling of the present invention also include inhibitory peptides. Suitable inhibitory peptides of the present invention are short peptides based on the sequence of human GM-CSF that exhibit inhibition of GM-CSF binding and direct biological antagonist activity. The amino acid sequence of human GM-CSF from which inhibitory peptides are derived is provided below as SEQ ID NO: 2

```
  1    mwlqsllllg  tvacsisapa  rspspstqpw  ehvnaiqear
       rllnlsrdta  aemnetvevi 61    semfdlqept  clqtrlelyk  qglrgsltkl  kgpltmmash
       ykqhcpptpe  tscatqiitf 121    esfkenlkdf  llvipfdcwe  pvqe  (SEQ ID NO: 2)
```

In one embodiment of the present invention, the GM-CSF inhibitory peptides are a derivative of GM-CSF with a basic amino acid residue substitution (e.g., arginine or lysine) at position 21 of the mature peptide (i.e., amino acid residue 38 of SEQ ID NO: 2). Suitable inhibitory GM-CSF peptides comprising these substitutions are disclosed in U.S. Pat. No. 6,322,791 to Vadas et al., which is hereby incorporated by reference in its entirety). Other suitable inhibitory peptides include peptides comprising amino acid residues 17-31 (the A helix of GM-CSF), which inhibit high affinity receptor binding activity, and peptides comprising amino acid residues 54-78 (B and C helices of GM-CSF), which inhibit low affinity receptor binding (see VonFeldt et al., "Development of GM-CSF Antagonist Peptides," Pept. Res. 8(1):20-27 (1995), which is hereby incorporated by reference in its entirety). GM-CSF antagonist peptides derived from the carboxy terminus of GM-CSF as disclosed by U.S. Pat. No. 5,475,087 to Seelig, which is hereby incorporated by reference in its entirety, are also suitable for use in the methods of the present invention. Cyclic peptide GM-CSF mimics with GM-CSF receptor antagonist activity are also suitable peptides for use in the present invention (see Monfardini et al., "Rational Design of Granulocyte-Macrophage Colony-Stimulating Factor Antagonist Peptides," J. Biol. Chem. 271(6):2966-71 (1996), which is hereby incorporated by reference in its entirety). Other suitable GM-CSF mimetics having antagonistic activity that are suitable for use in the methods of the present invention are described in Monfardini et al., "Structure-Based Design of Mimetics for Granulocyte-Macrophage Colony Stimulating Factor (GM-CSF)," Curr. Pharm. Des. 8(24):2185-99 (2002), which is hereby incorporated by reference in its entirety.

In another embodiment of the present invention, the therapeutic agent that inhibits GM-CSF activity or MDSC activity is an antibody. An antibody of the present invention encompasses any immunoglobulin molecule that specifically binds to an epitope of GM-CSF or a cell surface antigen, epitope, or protein that is specifically expressed on MDSCs. Suitable "epitopes" encompass a region or regions of the GM-CSF protein and a region or regions of MDSC cell surface antigens that are recognized by an isolated antibody and are involved in mediating the binding interaction between GM-CSF and its receptor, involved in mediating the downstream molecular signaling pathway triggered by the GM-CSF receptor binding, or are involved in mediated MDSC immunosuppressive activity. As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies, antibody fragments (e.g., Fv, Fab, F(ab)2, diabodies, triabodies, minibodies, etc.), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Huston et al., "Protein Engineering of Antibody Binding Sites: Recovery of Specific Activity in an Anti-Digoxin Single-Chain Fv Analogue Produced in Escherichia coli," Proc Natl Acad Sci USA 85:5879-5883 (1988); Bird et al, "Single-Chain Antigen-Binding Proteins," Science 242:423-426 (1988), which are hereby incorporated by reference in their entirety).

The present invention also encompasses the use of bispecific humanized antibodies or bispecific antigen-binding fragments (e.g., F(ab')2) which have specificity for GM-CSF or the GM-CSF receptor and a molecule expressed on a target tumor cell (e.g., pancreatic tumor cell). Techniques for making bispecific antibodies are known in the art (Brennan et al., "Preparation of Bispecific Antibodies by Chemical Recombination of Monoclonal Immunoglobulin G1 Fragments," Science 229:81-3 (1985); Suresh et al, "Bispecific Monoclonal Antibodies From Hybrid Hybridomas," Methods in Enzymol. 121:210-28 (1986); Traunecker et al., "Bispecific Single Chain Molecules (Janusins) Target Cytotoxic Lymphocytes on HIV Infected Cells," EMBO J. 10:3655-3659 (1991); Shalaby et al., "Development of Humanized Bispecific Antibodies Reactive with Cytotoxic Lymphocytes and Tumor Cells Overexpressing the HER2 Protooncogene," J. Exp. Med. 175:217-225 (1992); Kostelny et al, "Formation of a Bispecific Antibody by the Use of Leucine Zippers," J. Immunol. 148: 1547-1553 (1992); Gruber et al., "Efficient Tumor Cell Lysis Mediated by a Bispecific Single Chain Antibody Expressed in Escherichia coli," J. Immunol. 152:5368-74 (1994); and U.S. Pat. No. 5,731,168 to Carter et al., which are hereby incorporated by reference in their entirety).

Suitable GM-CSF antibodies and methods of making the same are disclosed in U.S. Pat. No. 5,475,087 to Seelig, U.S. Patent Application Publication No. 2010/0272730 to Sass et al., and U.S. Patent Application Publication No. 2011/0104172 to Plater-Zyberk et al., which are hereby incorporated by reference in their entirety. In one embodiment the antibodies of the present invention have neutralizing activity. U.S. Patent Application Publication No. 2010/0297135 to Mackay et al., which is hereby incorporated by reference in its entirety, discloses neutralizing epitopes of GM-CSF and corresponding neutralizing antibodies that are suitable for use in the present invention. A particularly suitable antibody for use in the methods of the present invention is MOR103 (MorphoSys, AG), a human monoclonal IgG1 antibody targeting GM-CSF (see U.S. Pat. No. 7,867,495 to Steidl et al., which is hereby incorporated by reference in its entirety).

Suitable antibodies for inhibiting MDSC immunosuppressive activity include, without limitation, antibodies that recognize Gr-1 (granulocyte-differentiation antigen-1) and abrogate myeloid-derived suppressor cell activity (see e.g., Ribechini et al., "Gr-1 Antibody Induces STAT Signaling, Macrophage Marker Expression and Abrogation of Myeloid-Derived Suppressor Cell Activity in BM Cells," Eur. J. Immunol. 39(12):3538-51 (2009), which is hereby incorporated by reference in its entirety), anti-CD80 antibodies (U.S. Patent Application Publication No. 2010/0203010 to Hariharan et al., which is hereby incorporated by reference in its entirety), and Tim-3 antibodies (U.S. Patent Application Publication No. 2011/0059106 to Kuchroo et al., which is hereby incorporated by reference in its entirety).

It may be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention also encompasses the nucleic acid molecules that encode the GM-CSF or MDSC antibodies of the invention. The nucleic acids may be present in whole cells, in a cell lysate, or in a partially purified or substantially pure form (i.e., purified away from other cellular components or other contaminants).

Nucleic acids encoding the antibodies of the present invention can be obtained using standard molecular biology techniques. For antibodies expressed by hybridomas, cDNAs encoding the light and heavy chains of the antibody made by the hybridoma can be obtained by standard PCR amplification or cDNA cloning techniques. For antibodies obtained from an immunoglobulin gene library (e.g., using phage display techniques), the nucleic acid encoding the antibody can be recovered from the library.

Preferred nucleic acid molecules of the invention are those encoding the VH and VL sequences of GM-CSF or MDSC monoclonal antibodies. Once DNA or cDNA fragments encoding VH and VL segments are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat et al., Sequences of Proteins of Immunological Interest, 5th ed., U.S. Department of Health and Human Services, NIH Publication No. 91-3242 (1991), which is hereby incorporated by reference in its entirety) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region. The sequences of human light chain constant region genes are known in the art (see e.g., Kabat et al., Sequences of Proteins of Immunological Interest, 5th ed., U.S. Department of Health and Human Services, NIH Publication No. 91-3242 (1991), which is hereby incorporated by reference in its entirety) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker such that the VH and VL sequences can be expressed as a contiguous single-chain protein, with the VH and VL regions joined by the flexible linker (see e.g., Bird et al., "Single Chain Antigen-Binding Proteins," *Science* 242:423-426 (1988); Huston et al., "Protein Engineering of Antibody Binding Sites: Recovery of Specific Activity in an Anti-Digoxin Single-Chain Fv Analogue Produced in *Escherichia coli,*" *Proc. Natl. Acad. Sci. USA* 85:5879-5883 (1988); McCafferty et al., "Phage Antibodies: Filamentous Phage Displaying Antibody Variable Domains," *Nature* 348: 552-554 (1990), which are hereby incorporated by reference in their entirety).

Other suitable inhibitors of MDSC immunosuppressive activity that are known in the art and are suitable for use in the methods of the present invention include phosphodiesterase-5 inhibitors, e.g., sildenafil, tadalafil, and vardenafil (see Serafina et al., "Phosphodiesterase-5 Inhibition Augments Endogenous Antitumor Immunity by Reducing Myeloid-Derived Suppressor Cell Function," *J. Exp. Med.* 203(12):2691-2702 (2006), which is hereby incorporated by reference in its entirety), and receptor tyrosine kinase inhibitors, such as, sunitinib (see Ko et al., "Direct and Differential Suppression of Myeloid-Derived Suppressor Cell Subsets by Sunitinib Is Compartmentally Constrained," *Cancer Res.* 70(9):3526-36 (2010), which is hereby incorporated by reference in its entirety).

In one embodiment of the present invention, targeted inhibition of GM-CSF and MDSC activity or recruitment in an individual is desired. In accordance with this embodiment, the GM-CSF inhibitors are targeted to cancer cells directly, thereby inhibiting GM-CSF expression and release by cancer cells, but not by normal, non-cancerous cells. Likewise, the MDSC inhibitor is preferably targeted to MDSCs only, so as to prevent non-specific side-effects of the inhibitors. To achieve selective inhibition of GM-CSF and/or MDSC in the tumor and surrounding tumor microenvironment, the agent is administered directly to the tumor site (i.e., direct tumor injection). The GM-CSF and/or MDSC inhibitor may be housed in a targeted delivery vehicle (suitable delivery vehicles are described infra). In yet another embodiment, selective targeting of the GM-CSF and/or MDSC inhibitor is achieved by coupling the inhibitor or the delivery vehicle containing the inhibitor to a targeting ligand for directed delivery of the inhibitor.

In accordance with this aspect of the invention, ligand directed delivery of the inhibitor is achieved using a cancer cell specific ligand targeting strategy. Suitable ligand directed cancer cell targeting systems are known in the art and include, without limitation, Eph-ligand based delivery (see U.S. Patent Publication No. 2010/0240594 to Pellecchia et al., which is hereby incorporated by reference in its entirety), vasoactive intestinal peptide, somatostatin, gastrin releasing peptide, bombesin, or substance P ligand based delivery systems (see U.S. Patent Publication No. 2010/ 0184651 to Maithal et al., which is hereby incorporated by reference in its entirety), urokinase, urokinase A chain, epidermal growth factor (EGF), transforming growth factor-alpha (TGFα), insulin-like growth factor, interleukin-4 (IL-4), interleukin-6 (IL-6), platelet-derived growth factor (PDGF), fibroblast growth factor (FGF), laminin, vascular endothelial growth factor (VEGF), and annexin V ligand based delivery systems (see U.S. Patent Publication No. 2005/0036984 to Harrison et al., which is hereby incorporated by reference in its entirety). In addition, a ligand for nucleophosmin, HSC70, BIP, Grp75, PDI, PDI ER60 precursor, HSP60, TCP-1ε, ERp29, HSP27, vimentin, α-internexin, cytokeratin 8, β-actin, γ-actin, β-tubulin, nm23-H1, valosin containing protein, tumor protein D52-like 2, ASF-2, hnRNPK, hnRNPC, 24.1D5 antigen, hnRNPA/B, Eukaryotic Elongation Factor 1δ Isoform 2, AU-rich element RNA binding protein, Rad 23 homologue B, annexin I, prohibitin, ubiquilin 1, or thioredoxin peroxidase 4, which are all surface markers for neoplastic cells (see U.S. Patent Publication No. 2007/0122414 to Georges et al., which is hereby incorporated by reference in its entirety), can also be used to target delivery of a GM-CSF inhibitor of the invention to cancer cells. Other cancer specific targeting peptides are disclosed by U.S. Patent Publication No. 2004/0102382 to Schughart et al., which is hereby incorporated by reference in its entirety.

In one embodiment of the present invention, the cancer to be treated is pancreatic cancer. In accordance with this embodiment, the GM-CSF inhibitor can be targeted to cancerous pancreatic cells using an anti-claudin or anti-mesothelin targeting moiety as described by May et al., "Enhancing Silicon Quantum Dot Uptake by Pancreatic Cancer Cells Via Pluronic® Encapsulation and Antibody Targeting," J. Solid Tumors 2(3): 24-37 (2012), which is hereby incorporated by reference in its entirety. Other cancerous pancreatic cell targeting moieties include interleukin-4 (Kawakami et al., "Targeting Interleukin-4 Receptors for Effective Pancreatic Cancer Therapy," Cancer Res. 62: 3575-80 (2002), which is hereby incorporated by reference in its entirety), and fucose (e.g., L-fucose) (Yoshida et al., "Targeting Anticancer Drug Delivery to Pancreatic Cancer Cells Using a Fucose-Bound Nanoparticle Approach," PLOS 7(7):e39545 (2012), which is hereby incorporated by reference in its entirety).

In accordance with the methods of the present invention, administering a GM-CSF or MDSC inhibitor to a subject can be carried out concurrently with other therapeutic approaches, i.e., the agent is administered as part of a combination therapy. Accordingly, in one embodiment of the invention, the agent is administered in combination with one or more additional cancer therapeutics such as, a chemotherapeutic, radiation (e.g., external beam radiation therapy or brachytherapy), an anti-angiogenic therapeutic, a stromal inhibitor, an immune-enhancing agent or an immunotherapeutic agent, a Ras inhibitor, and an extracellular matrix protein inhibitor.

Suitable chemotherapeutic agents for combination therapies include, without limitation, nucleoside analogs (e.g., gemcitabine (2'2'-difluorodeoxycytidine)), alkylating agents (e.g., chlorambucil, cyclophosphamide, CCNU, melphalan, procarbazine, thiotepa, BCNU, and busulfan), antimetabolites (e.g., methotraxate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic therapeutics suitable for use in a combination therapy approach with a GM-CSF or MDSC inhibitor of the invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist (e.g., Erlotinib), or any combination thereof. A number of suitable small molecule angiogenic inhibitors are known in the art or are under clinical development (see e.g., Wu et al., "Anti-Angiogenic Therapeutic Drugs for the Treatment of Human Cancer," J Cancer Molecules 4(2):37-45 (2008), which is hereby incorporated by reference in its entirety). The angiogenic inhibitors include, without limitation, Gefitinib (an ErbB inhibitor), Lapatinib (a dual ErbB1/ErbB2 inhibitor), Erlotinib, Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR Kit, Flt3, Tet and CSF1R inhibitor), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody). Other anti-angiogenic as well as anti-stromal agents suitable for use in a combination therapy comprising a GM-CSF or MDSC inhibitor of the present invention are disclosed in Bissell et al., "Why Don't We Get More Cancer? A Proposed Role of the Microenvironment in Restraining Cancer Progression," Nat. Med. 17(3):320-329 (2011), which is hereby incorporated by reference in its entirety.

Suitable anti-Ras therapeutic agents for use in combination with a GM-CSF or MDSC inhibitor of the present invention include, without limitation, S-trans, transfarnesylthiosalicylic acid (FTS), a non-toxic, specific Ras antagonist (see Weisz et al., "A New Functional Ras Antagonist Inhibits Human Pancreatic Tumor Growth in Nude Mice," Oncogene 18(16):2579-2588 (1999), which is hereby incorporated by reference in its entirety), and the farnesyltransferase inhibitor, FTI-277, (see Bernhard et al., "The Farnesyltransferase Inhibitor FTI-277 Radiosensitizes H-ras-transformed Rat Embryo Fibroblasts," Cancer Research 56: 1727-1730 (1996), which is hereby incorporated by reference in its entirety).

Suitable immunotherapeutic agents for use in combination with a GM-CSF or MDSC inhibitor include both peptide and whole tumor cell vaccines. With regard to peptide immunotherapeutics, mutant K-ras peptide, MUC1 peptide, telomerase peptide, and survivin peptide vaccines have demonstrated immunotherapeutic utility, particularly in patients with pancreatic cancers. Accordingly, these peptide vaccines are suitable for use in combination with a GM-CSF or MDCS inhibitor in carrying out the methods of the present invention. In another embodiment of the present invention allogeneic or autologous whole tumor cell-based vaccines are administered in combination with GM-CSF or MDCS inhibitor when carrying out the methods of the present invention.

In an alternative embodiment of the invention, the agent is administered as a part of an adjuvant therapy regime. In particular, this involves chemotherapy, hormone therapy, radiation therapy, immunotherapy, or a targeted therapy together with an agent that inhibits GM-CSF or MDSC activity prior to and/or after surgery.

Another aspect of the present invention relates to a method of preventing or delaying tumor formation in a subject. This method involves selecting a subject susceptible to tumor formation and administering to the selected subject an agent that inhibits or suppresses GM-CSF and/or MDSC activity under conditions effective to prevent tumor formation in the subject.

In one embodiment of this aspect of the present invention, the subject is susceptible to the formation of a pancreatic tumor. Subjects that are susceptible to the formation of a pancreatic tumor include those individuals having a genetic predisposition to tumor development. For example, individuals carrying germ-line mutations in BRCA2, BRCA1, p16(CDKN2A), PRSS1, STK11/LKB1, hMLH1, hMSH2, FANC-C, and FANC-G have an increased risk of developing pancreatic cancer (see Maitra and Hruban, "Pancreatic Cancer," *Annu. Rev. Pathol.* 3:157-188 (2008), which is hereby incorporated by reference in its entirety). Other subjects that are susceptible to the formation of a pancreatic tumor include subjects who have had or have acute or chronic pancreatitis, particularly subjects having developed a pancreatic abscess or a pancreatic pseudocyst as a complication of pancreatitis. Susceptible patients also include subjects who have conditions associated with the development of acute or chronic pancreatitis, such as, autoimmune disorders, blockage of the pancreatic duct or common bile duct, cystic fibrosis, hyperparathyroidism, and hypertriglyceridemia. In addition, subjects using certain medications that have been linked to the development of pancreatitis are also susceptible to pancreatic tumor formation and suitable for treatment in accordance with the methods of the present invention. These medications include estrogens, corticosteroids, thazide diuretics, and azathioprine.

Suitable inhibitory agents of GM-CSF and MDSC include those described supra. In accordance with this aspect of the invention, direct or targeted administration of the GM-CSF and MDSC inhibitors may be desirable. Accordingly, the inhibitory agents are administered directly to the target organ, e.g., to the pancreas, by direct injection or coupled to a pancreatic cell targeting moiety, such as claudin-1, interleukin-4, or mesothelin as described supra.

In accordance with the methods of the present invention, the mode of administering the GM-CSF inhibitory agent and/or MDSC inhibitory agent, including the use of suitable delivery vehicles, to a subject at risk of developing a tumor, or a subject having a tumor will vary depending on the type of therapeutic agent (e.g., nucleic acid molecule, inhibitory peptide, antibody, or small molecule).

Pharmaceutical compositions containing GM-CSF and MDSC inhibitory agents that are suitable for use in the methods of the present invention may include a pharmaceutically acceptable carrier, one or more active agents, and a suitable delivery vehicle. Suitable delivery vehicles include, but are not limited to viruses, bacteria, biodegradable microspheres, microparticles, nanoparticles, liposomes, collagen minipellets, and cochleates.

In one embodiment of the present invention, the delivery vehicle is a liposome delivery vehicle. Liposomes are vesicles comprised of one or more concentrically ordered lipid bilayers which encapsulate an aqueous phase. A liposome which includes a GM-CSF and/or MDSC inhibitor is contacted with a population of target cancer cells under conditions effective for delivery of the inhibitory agent to the cancer cell or to MDSCs. The liposome delivery system can be made to accumulate at a target organ, tissue, or cell via active targeting (e.g., by incorporating an antibody or other ligand on the surface of the liposomal vehicle). This can be achieved using antibodies or ligands specific for an appropriate cancer cell marker as described supra.

Different types of liposomes can be prepared according to Bangham et al., "Diffusion of Univalent Ions across the Lamellae of Swollen Phospholipids," *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety. These liposomes can be produced such that they contain, in addition to a GM-CSF and/or MDSC inhibitor, other therapeutic agents, such as anti-inflammatory agents, chemotherapeutic agents, or immune-enhancing agents (e.g., IL-2 or interferon alpha), which would also be released at the target site (e.g., Wolff et al., "The Use of Monoclonal AntiThy1-IgG1 for the Targeting of Liposomes to AKR-A Cells in vitro and in vivo," *Biochem. Biophys. Acta* 802:259 (1984), which is hereby incorporated by reference in its entirety).

In another embodiment of the present invention, the delivery vehicle is a viral vector. Viral vectors are particularly suitable for the delivery of inhibitory nucleic acid molecules, such as siRNA or shRNA molecules targeting GM-CSF. Suitable viral vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993), which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Viral vectors are administered to a subject by, for example, intravenous injection or local administration (see U.S. Pat. No. 5,328,470 to Nabel et al., which is hereby incorporated by reference in its entirety). The pharmaceutical preparation of the gene therapy vector can include the gene therapy vector in an acceptable diluent, or can comprise a slow release matrix in which the gene delivery vehicle is imbedded As an alternative to viral-vector delivery, nucleic acid molecule inhibitors (e.g., siRNA molecule) can be encapsulated in a lipid formulation to form a nucleic acid-lipid particle as described in Semple et al., "Rational Design of Cationic Lipids for siRNA Delivery," *Nature Biotech.* 28:172-176 (2010) and WO2011/034798 to Bumcrot et al., WO2009/111658 to Bumcrot et al., and WO2010/105209 to Bumcrot et al., which are hereby incorporated by reference in their entirety.

In another embodiment of the present invention, the delivery vehicle is a nanoparticle. A variety of nanoparticle delivery vehicles are known in the art and are suitable for delivery of a GM-CSF and/or MDSC inhibitor of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In practicing the methods of the present invention, the administering step is carried out to achieve cancer cell specific inhibition of GM-CSF release and activity, and such administration can be carried out systemically or via direct or local administration, i.e., to a tumor site. By way of example, suitable modes of systemic administration include, without limitation, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Suitable modes of local administration include, without limitation, catheterization, implantation, direct injection, dermal/transdermal application, stenting, or portal vein administration to relevant tissues, or any other local administration technique, method or procedure, as is generally known in the art.

Therapeutic agents of the present invention are formulated in accordance with their mode of administration. For oral administration, for example, the therapeutic agents of the present invention are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

The therapeutic agents of an oral formulation may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: Enzymes as Drugs, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The therapeutic agents of the present invention may also be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the therapeutic agents of the present invention, for the treatment or the prevention of tumor growth or progression vary depending upon many different factors, including type and stage of tumor, mode of administration, target site, physiological state of the patient, other medications or therapies administered, and physical state of the patient relative to other medical complications. Treatment dosages need to be titrated to optimize safety and efficacy.

Another aspect of the present invention is directed to a method of diagnosing a subject as having or not having cancer. This method involves obtaining a sample from a subject and measuring GM-CSF levels and/or MDSC levels in the sample. The measured GM-CSF and/or MDSC levels in the sample are compared to GM-CSF and/or MDSC levels, respectively, in a reference sample, and the subject is diagnosed as having or not having cancer based on this comparison.

In accordance with this aspect of the present invention, the sample from the subject may comprise a blood or serum sample. In one embodiment, the reference sample is a corresponding sample obtained from the subject to be diagnosed at an earlier time point, i.e., when the subject was known to be cancer-free.

In one embodiment of this aspect of the invention, measuring GM-CSF levels in the sample involves determining the level of GM-CSF protein expression and/or the level of GM-CSF mRNA expression in a sample. Methods of detecting and quantifying protein and mRNA expression levels in a sample are well known in the art.

mRNA from a subject can be isolated and prepared from tissue or cell samples using methods known in the art. The RNA preparation must produce enzymatically manipulatable mRNA or analyzable RNA. Total RNA and mRNA may be isolated using known methods in the art, including the guanidinium isothiocyanate-ultracentrifugation method, the guanidinium and phenol-chloroform method, the lithium chloride-SDS urea method, or the oligo (dT) cellulose method. Total isolated RNA can be used to generate first strand copy DNA (cDNA) using any known procedure in the art, for example, using random primers, oligo-dT primers, or random-oligo-dT primers. The cDNA is then used as a template for a first round amplification reaction or for a quantitative PCR reaction depending on target or sample abundance. The first round PCR amplification is performed with a primer set, including forward and reverse primers that are specific for the target gene of interest (i.e., GM-CSF). Following the first round of amplification, a cleaned portion of the reaction product is used for quantitative analysis. Quantitative real-time PCR protocols typically rely on fluorescent detection of product formation following the extension phase of the reaction cycle. Typical fluorescent approaches for quantitative PCR are based on a fluorescent reporter dyes such as SYBR green, FAM, fluorescein, HEX, TET, TAMRA, etc. and quencher dyes such as DABSYL, Black Hole, etc. Systems, such as Molecular Beacons (Integrated DNA Technologies, Coralville, Iowa), Taqman® Probes (Applied Biosystems, Foster City, Calif.), LNA or MGB Probes, Scorpion® Primers (DxS Ltd., Manchester, UK), AmpliFluor, Plexor, or Lux primers are also well known in the art of quantitative gene analysis. Examples of methods and reagents related to real time probes can be found in U.S. Pat. Nos. 5,925,517, 6,103,476, 6,150,097, and 6,037,130 all to Tyagi et al., which are hereby incorporated by reference in their entirety.

Quantitative gene expression can be expressed as absolute copy number or as relative gene expression. Both methods utilize a standard curve from which to accurately obtain quantitative data from. Alternatively, relative gene expression can also be calculated using the Comparative $C_T$ Method as described in the ABI Prism 7700 Sequence Detection System User Bulletin #2 which is hereby incorporated by reference in its entirety. The Comparative $C_T$ method is similar to the standard curve method, except it uses an arithmetic formula to calculate the relative gene expression data. A detailed description of absolute and relative gene expression quantitation is provided in the ABI Prism 7700 Sequence Detection System User Bulletin #2, which is hereby incorporated by reference in its entirety. An increase in the GM-CSF mRNA expression in the test sample compared to the reference sample indicates the presence of cancer.

Methods for detecting and quantifying protein expression in a sample are readily known in the art. Sample protein from the subject can be isolated and prepared from a sample using standard preparation methods known in the art. For example, cells can be lysed in buffer containing a detergent, such as sodium dodecyl sulfate (SDS), and a cocktail of protease inhibitors. Protein yield can be determined using the Bradford Assay or any variation of the method known in the art. Assessing the level of expression of a target protein within a sample can be performed by various techniques known in the art, For example, assessing the level of expression can involve analyzing one or more proteins by two-dimensional gel electrophoresis, mass spectroscopy, high performance liquid chromatography (HPLC), fast protein liquid chromatography, multi-dimensional liquid chromatography followed by tandem mass spectrometry, or protein chip expression analysis. Other techniques involve contacting the sample with one or more detectable reagents that is suitable for measuring protein expression, e.g., a labeled antibody having binding specificity for GM-CSF or a primary antibody having binding specificity for GM-CSF used in conjunction with a secondary antibody, and measuring protein expression level based on the level of detectable reagent in the sample after normalizing to total protein in the sample. Suitable methods for detecting protein expression level in a sample, e.g., a blood or serum sample, that are commonly employed in the art include, for example and without limitation, western blot, immunoprecipitation, enzyme-linked immunosorbent assay (ELISA), radioimmunoassay (RIA), or fluorescent activated cell sorting (FACS). The measured protein expression level in the sample is compared to the protein expression level measured in a reference sample and a diagnosis of the presence or absence of cancer based on this comparison is made. An increase in the GM-CSF protein expression in the test sample compared to the reference sample indicates the presence of cancer.

In another embodiment of this aspect of the invention, measuring GM-CSF levels in a sample is achieved by measuring the GM-CSF levels in serum from the subject, using, for example, an enzyme-linked immunosorbent assay (ELISA) (see e.g., Mroczko et al., "Hematopoietic Cytokines in the Sera of Patients with Pancreatic Cancer," *Clin.*

*Chem. Lab. Med.* 43(2):146-150 (2005), which is hereby incorporated by reference in its entirety).

In accordance with this aspect of the invention, measuring MDSC levels in the sample involves counting the number of MDSCs in a tissue or serum sample from the subject. Counting the number of MDSCs in a sample can be achieved by immunocytochemical or immunohistochemical staining of a tissue or cell sample using one or more cell specific markers, e.g., CD11b, CD15, CD33, CD34, CD14, HLA-DR, and counting the number of labeled cells in the sample or quantifying the intensity of cell specific label in the sample. Alternatively, MDSC cells in a serum or blood sample from the subject can be labeled using an antibody recognizing one or a combination of cell specific antigen/ligands, and counted using flow cytometry analysis. In one embodiment, MDSC levels are determined by counting CD11b$^+$CD33$^+$CD34$^+$CD14$^-$HLA-DR$^-$ cells in a sample. In another embodiment of the present invention, MDSC levels are determined by counting CD14$^+$HLA-DR$^{-/low}$ cells in a sample from the subject.

In accordance with this aspect of the invention, an increase in GM-CSF level and/or an increase in MDSC level in the sample from the subject compared to the GM-CSF level and/or MDSC level in the reference sample indicates the subject has cancer. An increased level of GM-CSF and MDSC recruitment in the sample from the subject is further indicative of an oncogene mediated cancer, e.g., a Ras-mediated cancer, such as pancreatic cancer.

A positive diagnosis of cancer based on enhanced levels of GM-CSF or enhanced numbers of MDSCs can help guide and determine a suitable treatment regimen. For example, recombinant GM-CSF is widely used as an adjuvant therapy for a variety of human neoplasms. Its therapeutic utility, however, has had mixed results. As described herein, in cancers, such as pancreatic cancer, where an enhanced level of GM-CSF promotes tumor growth through the recruitment of MDSC, GM-CSF should not be administered as an adjuvant therapy. In these cancers, GM-CSF inhibition and/or MDSC inhibition in accordance with the methods of the present invention is the preferred course of treatment.

Accordingly, another aspect of the present invention is directed to a method of treating a subject having cancer. This method involves measuring GM-CSF levels and/or MDSC levels in a cancerous sample from the subject and comparing the measured GM-CSF and/or MDSC levels in the sample to GM-CSF and/or MDSC levels, respectively, in a reference sample. This method further involves selecting a treatment for the subject having cancer based on the comparison and administering the selected treatment to the subject.

In accordance with this aspect of the present invention the sample may be a tissue, cell, blood, or serum sample. The reference sample GM-CSF and/or MDSC levels are baseline levels representing the level of GM-CSF expression or MDSC cell count in a sample obtained from a GM-CSF mediated tumor, a non-GM-CSF mediated tumor, or both. The reference sample level is a known level to which the measured level can be compared too to determine the type of tumor the subject has. Such a reference level may represent an average GM-CSF expression level or MDSC cell count, or a range thereof, obtained from a cohort of individuals having a GM-CSF mediated tumor or a non-GM-CSF mediated tumor. In accordance with this embodiment of the present invention, when the GM-CSF expression level or MDSC count in a sample from a subject to be treated is similar to the GM-CSF expression level or MDSC count in a sample from a GM-CSF mediated tumor or greater than the GM-CSF expression level of MDSC count in a sample from a non-GM-CSF mediated tumor than the selected treatment for the subject is a GM-CSF inhibitor and/or a MDSC inhibitor.

In another embodiment of the present invention, the reference level is the level of GM-CSF expression or MDSC count in a corresponding sample from the subject at an earlier timepoint. In accordance with this embodiment, when there is an increase in the GM-CSF expression level or MDSC count in the subject's sample relative to the reference sample GM-CSF expression level or MDSC count, the selected treatment comprises a GM-CSF inhibitor and/or a MDSC inhibitor. Methods of determining the levels of GM-CSF expression and MDSC count in a tissue or serum sample from a subject are described supra. Suitable GM-CSF and MDSC inhibitors and modes of administration are also described supra.

Another aspect of the invention relates to a method of producing an orthotopic non-human mammal model of pancreatic cancer. This method involves introducing oncogenic pancreatic ductal epithelial cells into pancreatic tissue of a recipient non-human mammal under conditions effective for the formation of pancreatic cancer, thereby producing an orthotopic non-human mammal model of pancreatic cancer.

A related aspect of the present invention is directed to an orthotopic non-human mammal model of pancreatic ductal adenocarcinoma that comprises pancreas-specific mutational activation of Kras. As described herein, this orthotopic non-human mammal model comprises primary pancreatic epithelial cells that histologically progress to intraepithelial neoplasia (PanIN) in a series of steps that mimic the histological progress in human pancreatic epithelial cells in vivo (see Maitra and Hruban, "Pancreatic Cancer," *Annu. Rev. Pathol.* 3:157-188 (2008), which is hereby incorporated by reference in its entirety).

In accordance with these aspects of the invention, the oncogenic pancreatic ductal epithelial cells comprise a mutationally activated Ras oncogene, e.g., a Kras oncogene. In one embodiment of the invention, the mutationally activated Kras oncogene encodes a G→D amino acid substitution at an amino acid residue corresponding to amino acid residue 12 of SEQ ID NO: 3 (Kras$^{G12D}$).

```
  1    mteyklvvvg aggvgksalt iqliqnhfvd eydptiedsy
       rkqvvidget clldildtag 61    geeysamrdq ymrtgegflc vfainntksf edihhyreqi
       krvkdsedvp mvlvgnkcdl 121    psrtvdtkqa qelarsygip fietsaktrq gvddafytlv
       reirkhkekm skdgkkkkkk 181    srtrctvm (SEQ ID NO: 3)
```

Methods of isolating pancreatic ductal epithelial cells are known in the art (see e.g., Agbunag et al., "Pancreatic Duct Epithelial Cell Isolation and Cultivation in Two-Dimensional and Three-Dimensional Culture Systems," *Meth. Enzym.* 407:703-710 (2006), which is hereby incorporated by reference in its entirety). Methods of introducing a Kras$^{G12D}$ allele into the cultured cells and tissue are disclosed in Lee et al., "Oncogenic KRas Suppresses Inflammation-Associated Senescence of Pancreatic Ductal Cells," *Cancer Cell* 18:448-458 (2010) and Monticone et al., "Gene Expression Deregulation by KRAS G12D and G12V in a BRAF V600E Context," *Mol. Cancer* 7:92 (2008), and Jackson et al., "Analysis of Lung Tumor Initiation and Progression Using Conditional Expression of Oncogenic K-ras," *Genes Dev.* 15(24):3243-8 (2001), which are hereby incorporated by reference in their entirety. Orthotopic implantation of the Kras$^{G12D}$-PDEC into a non-human mammal is described infra in the Examples.

The orthotopic model of the present invention can be any non-human mammal, e.g., dog, cat, monkey, pig, etc. In a preferred embodiment of this aspect of the invention, the orthotopic model of the invention is a rodent, e.g., a mouse or rat.

EXAMPLES

The following examples are provided to illustrate embodiments of the present invention but they are by no means intended to limit its scope

Example 1

Animal Models

The LSL-Kras$^{G12D}$ and p48-Cre strains have been described previously (Jackson et al., "Analysis of Lung Tumor Initiation and Progression Using Conditional Expression of Oncogenic K-Ras," *Genes Dev.* 15:3243-3248 (2001), which is hereby incorporated by reference in its entirety). C57BL/6 mice were obtained from the Charles River Laboratories. For orthotopic implantation of PDEC, mice were anesthetized using ketamine/xylazine cocktail, and a small (7 mm) left abdominal side incision was made. PDEC (1×10$^6$ cells/mouse) were suspended in 50 μl of Matrigel (Becton Dickinson) diluted 1:1 with cold PBS and injected into the tail region of the pancreas using a 26-gauge needle. A successful injection was verified by the appearance of a fluid bubble without intraperitoneal leakage. The abdominal wall was closed with absorbable Vicryl RAPIDE sutures (Ethicon) and skin was closed with wound clips (Roboz). Mice were sacrificed at the indicated time points, and grafts were measured and processed for histology or flow cytometry.

Example 2

Isolation, Culture, and Infection of PDEC

Isolation, culture, and adenoviral infection of PDECs were carried out as previously described (Agbunag et al., "Pancreatic Duct Epithelial Cell Isolation and Cultivation in Two-Dimensional and Three-Dimensional Culture Systems," *Meth. Enzym.* 407:703-710 (2006), and Lee et al., "Oncogenic Kras Suppresses Inflammation-Associated Senescence of Pancreatic Ductal Cells," *Cancer Cell* 18:448-458 (2010), which are hereby incorporated by reference in their entirety). Lentiviral vectors containing shRNAs directed against the GM-CSF gene (GM-sh1 and GM-sh2; clone ID TRCN0000054618 and TRCN0000054620) and control scrambled shRNA (scr) were obtained from Open Biosystems (pLKO.1, TRC Consortium). To generate lentiviral particles, HEK-293T cells were co-transfected with the vector, the packaging construct (pHR-CMV-dR8.2), and the envelope plasmid (pCMV-VSVG). Viral stocks were collected for 2 days, filtered through a 0.45 μm filter and concentrated using 100 MWCO Amicon Ultra centrifugal filters (Millipore). A multiplicity of infection of 15 was used for lentiviral infection of WT- or Kras$^{G12D}$-PDEC in the presence of 10 μg/ml Polybrene (Chemicon).

Example 3

Immunoblot Analysis

Cells were lysed in 1% Triton-X buffer (50 mM HEPES pH 7.4, 1% Triton X-100, 150 mM NaCl, 10% glycerol, 1 mM EGTA, 1 mM EDTA, 25 mM NaF, 1 mM Na vanadate, 1 mM phenylmethanesulfonyl fluoride (PMSF) and protease inhibitors). The following primary antibodies were used: mouse anti-HA (12CA5), mouse anti-vinculin (Sigma-Aldrich), rabbit anti-phospho-ERK (Cell Signaling), mouse anti-ERK (Cell Signaling), rabbit anti-phospho-AKT (Cell Signaling) and rabbit anti-AKT (Cell Signaling). After incubation with the secondary IRDye Alexa Fluor 680 goat anti-mouse antibody or 800 goat anti-rabbit antibody (Molecular Probes), the membranes were visualized with the Odyssey Infrared Imaging System (Li-Cor).

Example 4

Quantitative RT-PCR

Extraction and reverse transcription of total RNA from PDECs was performed using RNeasy mini kit (QIAGEN) and QuantiTect reverse transcription kit (QIAGEN), respectively. SYBR Green PCR Master Mix (USB) was used for amplification and the samples were run on the Stratagene Mx 3005P. Expression levels were normalized by GAPDH.

Example 5

Human Pancreas Specimens

The use of human tissue was reviewed and approved by the Institutional
Review Board of NYU School of Medicine and samples were obtained after informed consent. Sections (5 μm) were cut from formalin-fixed paraffin-embedded samples for the purpose of immunohistochemistry. Samples from 16 pancreatic adenocarcinomas, one chronic pancreatitis, one benign pancreatic cyst, one serous cystadenoma, and one intraductal papillary mucinous neoplasm were analyzed.

Example 6

Histology and Immunohistochemistry

Mouse pancreata were fixed overnight in 10% formalin (Fisher) and processed for paraffin-embedding. For histology, deparaffinized sections (6 μm) were stained with Harris hematoxylin and eosin (both from Sigma-Aldrich) followed by alcohol dehydration series and mounting (Permount, Fisher). Trichrome staining was performed at NYU School of Medicine Histopathology Core Facility. For immunohistochemistry, deparaffinized sections (6 μm) were rehydrated, quenched in 1% hydrogen peroxide/methanol for 15 minutes, and antigen retrieval was performed in 10 mM sodium citrate/0.05% Tween-20 (pH 6.0) for 15 minutes in a microwave oven. Blocking was done in 10% serum/1% BSA/0.5% Tween-20 for 1 hour at room temperature, followed by incubation with the primary antibodies diluted in 2% BSA overnight at 4° C. The following primary antibodies were used: rabbit anti-GFP (Cell Signaling), rabbit anti-GM-CSF (Novus Biologicals), rat anti-CD8 (53-6.7, BD Biosciences), rabbit anti-cleaved caspase-3 (Cell Signaling), rat anti-B220 (BD Biosciences) and rat anti-Gr1 (RB6-8C5, BD Biosciences). After incubating with secondary biotinylated antibodies and ABC solution (both from Vector Laboratories), sections were developed with 3,3'-diaminobenzidine tetrahydrochloride (Sigma-Aldrich). After counterstaining with Harris hematoxylin, slides were subjected to alcohol dehydration series and mounted with Permount. Slides were examined on a Nikon Eclipse 80i microscope

Example 7

Immunofluorescence

Mouse pancreata were embedded in OCT compound (Tissue-Tek) by snap freezing OCT-covered tissues in liquid nitrogen, and 8 μm sections were cut on a Leica microtome. After fixing the sections in 4% paraformaldehyde for 10 minutes on ice and permeabilizing with 0.25% Triton X-100 for 10 minutes on ice, sections were blocked with 10% serum/2% BSA/0.1% Tween-20 for 1 hour at room temperature. Incubation with primary antibodies diluted in 2% BSA/0.5% Tween-20 was performed overnight at 4° C. The following antibodies were used: rat anti-CD45 (BD Biosciences) and rat anti-CK19 (Troma III, Developmental Studies Hybridoma Bank). After incubating with Alexa Fluor-labeled secondary antibodies (Invitrogen) diluted in 1% BSA for 1 hr at room temperature, sections were stained for DAPI and mounted using polyvinyl alcohol mounting media with DABCO (Fluka). Slides were examined on a Zeiss Axiovert 200M microscope.

Example 8

Flow Cytometry

Cellular suspensions from the tissues were prepared as follows. Spleens were mechanically disrupted, suspended in 1%FBS/PBS, passed through a 70 μm strainer and treated with RBC lysis buffer (eBioscience). Pancreata were minced using sterile razor blades and incubated in 1.25 mg/ml collagenase type IV/0.1% soy bean trypsin inhibitor (Sigma-Aldrich) in RPMI for 15 minutes at 37° C. Cells were suspended in 1%FBS/PBS, passed through a 70 μm strainer, and treated with RBC lysis buffer. Single cell suspensions from spleens and pancreata were blocked with anti-CD16/CD32 antibody (Fc Block, BD Biosciences) for 5 minutes on ice, and labeled with the following antibodies: anti-CD45.2 (104), anti-CD3ε (500A2), anti-CD4 (RM4-5), anti-CD8α (53-6.7), anti-CD45R/B220 (RA3-6B2), anti-CD19 (1D3), anti-CD11b (M1/70), anti-Gr1 (RB6-8C5), anti-CD25 (PC61.5) (all from BD Biosciences). Staining for intracellular Foxp3 was performed using Mouse Regulatory T Cell Staining Kit (FJK-16, eBioscience). Dead cells were excluded by staining with Propidium Iodine (Sigma-Aldrich). Flow cytometry was performed on FACScan (BD Biosciences) at NYU School of Medicine Flow Cytometry Core Facility and data was analyzed using FlowJo software.

Example 9

Supernatant Collection and Cytokine Analysis

For cytokine analysis of PDEC cultures, cells were cultured in complete medium at a concentration of $1 \times 10^6$ cells/ml for 24 hours before supernatant harvest. For cytokine analysis of mouse pancreata, the tissues were harvested, weighed, minced with a sterile razor blade, and incubated in 500 μl of complete media for 24 hours before supernatant collection. Analysis of the cytokines was done with Milliplex Map Immunoassay (Millipore) and the Luminex 200 system (Luminex) according to manufacturer's instructions. Where indicated, mouse GM-CSF protein levels were determined by Mouse GM-CSF Quantikine ELISA Kit (R&D Systems). For analysis of GM-CSF levels in mouse sera, blood samples were collected retro-orbitally, and the samples were processed according to the manufacturer of the ELISA kit.

Example 10

Culture of Sorted Hematopoietic Progenitor Cells (HPC)

Bone marrow cells were isolated from C57B1/6 mice and HPC were sorted using Mouse Hematopoietic Stem and Progenitor Cell Isolation Kit (BD Biosciences), according to the manufacturer's instructions. Isolated HPCs were cultured in 6-well plates ($1 \times 10^5$ cells/well) for a total of 6 days. On day 0, either GM-CSF (10 ng/ml, Monoclonal Antibody Core Facility at Memorial Sloan-Kettering Cancer Center) or a 24 mm Transwell insert with a 0.4 μm pore size (Corning Life Sciences) containing $Kras^{G12D}$-PDEC ($2 \times 10^5$ cells/insert) were added directly to the top of well containing HPCs. On day 3, fresh cytokine or inserts with cells were added. Where indicated, HPC cultures were supplemented with either control IgG2a antibody (1 μg/ml, eBioscience) or anti-GM-CSF antibody (1 μg/ml MP1-22E9, eBioscience). For T cell proliferation assays, Gr1$^+$CD11$^+$ cells were sorted on day 6 of culture. Cellular purity was greater than 90%.

Example 11

Proliferation and Viability Assays

For in vitro T cell proliferation assays, splenic T cells suspended in complete RPMI medium were added to 96-well plates pre-coated with anti-CD3 antibody (BD Biosciences) at a density of $5 \times 10^4$ cells/well. Where indicated, anti-CD28 antibody (37.51, eBioscience) was added to T cells at a concentration of 1 μg/ml. Autologous Gr1$^+$CD11b$^+$ cells derived from co-culture of $Kras^{G12D}$-PDEC and HPC were irradiated and added directly to T cells ($5 \times 10^4$ Gr1$^+$CD11b$^+$ cells/well) 24 hours before adding BrdU reagent (Sigma-Aldrich). T cells were labeled by adding BrdU to the culture medium at a final concentration of 10 μM for 48 hours. Staining for BrdU was achieved using APC BrdU Flow Kit (BD Biosciences). Percentage of BrdU-positive T cells was determined by FACS analysis of CD3$^+$ BrdU$^+$ cells.

For $Kras^{G12D}$-PDEC growth assays, cells were seeded at a density of 2,000 cells/well of a 96-well plate. At indicated timepoints, cell culture medium was aspirated, the wells were washed with RPMI (without phenol red, BioWhittaker) and 0.5 mg/ml 3-[4,5-dimethylthiazol-2-yl]-2,5-diphenyl tetrazolium bromide (MTT; Sigma-Aldrich) was added for 2 hours at 37° C. The reagent was aspirated and 100 μl of DMSO was added to each well for 20 minutes at room temperature. Plates were read at an absorbance of 570 nm using a VERSAmax microplate reader (Molecular Devices). For the day 0 time-point, cells were treated with MTT reagent 2-hours post-plating.

Example 12

CD8 Depletion

Mice were depleted of CD8$^+$ T cells via intra-peritoneal injection of control rat IgG antibody (eBioscience) or anti- CD8a antibody at a concentration of 0.2 mg/mouse (53-6.72, Monoclonal Antibody Core Facility at Memorial Sloan-Kettering Cancer Center). Injections were administered every day for 3 days prior to orthotopic injection, and twice a week thereafter until the experimental end-point. The efficiency of CD8$^+$ T cell depletion was assessed by FACS of splenic tissues using anti-CD3 and anti-CD8 antibodies.

Example 13

Statistical Analyses

Data are presented as averages±standard deviations (SD). Quantification of GFP positivity was performed using ImageJ analysis. Data were analyzed by the Microsoft Excel or GraphPad Prism built-in t test (unpaired, two-tailed), and results were considered significant at $p<0.05$.

Example 14

Results and Discussion

To investigate the role of oncogenic Kras in modulating the host immune response in the course of pancreatic neoplasia, an orthotopic allograft system was established in which primary ductal epithelial cells (PDEC) isolated from LSL-Kras$^{G12D}$ knock-in mice were injected into the pancreata of syngeneic C57Bl/6 mice. Expression of the Kras$^{G12D}$ allele in these cells was induced prior to implantation by Cre-mediated recombination as previously described (Lee et al., "Oncogenic Kras Suppresses Inflammation-Associated Senescence of Pancreatic Ductal Cells," *Cancer Cell* 18:448-458 (2010), which is hereby incorporated by reference in its entirety), and, for the purpose of in situ identification, the cells were engineered to express green fluorescent protein (GFP) ("GFP-Kras$^{G12D}$-PDECs"). To minimize the possibility of a genetic drift, PDEC were propagated in culture only for a limited number of passages (<16). As illustrated in FIG. 1A, implanted Kras$^{G12D}$-PDEC formed ductal structures of heterogeneous size and architecture mostly resembling early PanIN lesions and reactive ducts. Notably, the grafts were characterized by a pronounced localized desmoplasia (Trichrome staining, FIG. 1A, far right) and the overt presence of CD45$^+$ immune cells (FIG. 1B). The same results were obtained using five independent PDEC isolates, indicating that GFP-Kras$^{G12D}$-PDEC implants possess an intrinsic capacity to invoke a robust stromal response. Sham injections had no apparent effect on the pancreatic parenchyma, ruling out the contribution of injury-induced inflammation to the observed immune response. GFP labeled wild-type PDEC ("GFP-WT-PDECs) failed to engraft consistent with their previously reported survival disadvantage relative to Kras$^{G12D}$-PDEC (FIG. 2A) (Lee et al., "Oncogenic Kras Suppresses Inflammation-Associated Senescence of Pancreatic Ductal Cells," *Cancer Cell* 18:448-458 (2010), which is hereby incorporated by reference in its entirety).

Figures 2C, 2D:
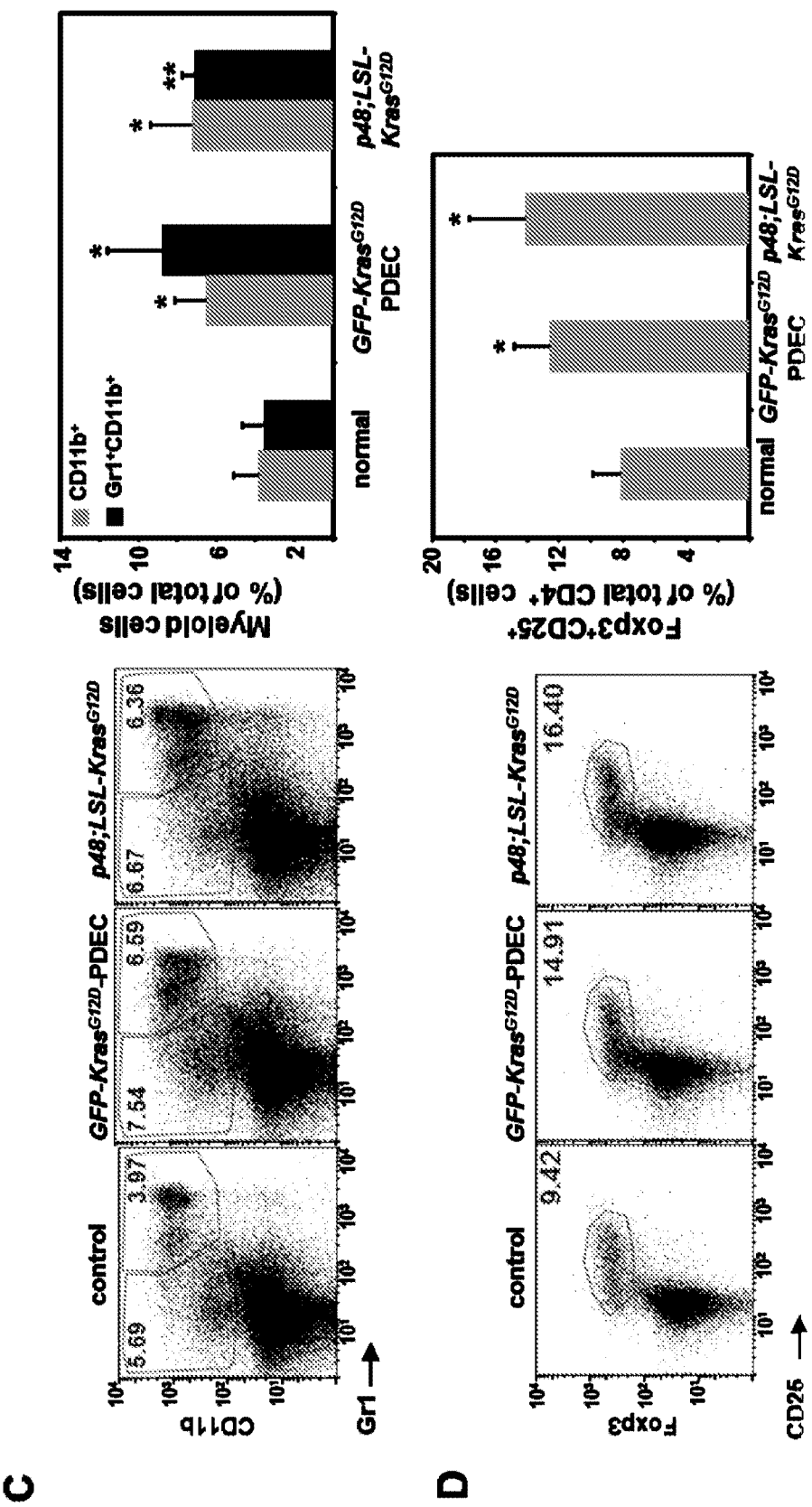

To ascertain whether the immunologic reaction evoked by Kras$^{G12D}$-PDEC in the orthogeneic system is physiologically relevant, flow cytometry analysis was used to compare the overall abundance and subtype distribution of immune cells in pancreata containing GFP-Kras$^{G12D}$-PDEC grafts and pancreata from LSL-Kras$^{G12D}$ p48-Cre mice (p48-Cre; LSL-Kras$^{G12D}$) (Hingorani et al., "Preinvasive and Invasive Ductal Pancreatic Cancer and its Early Detection in the Mouse," *Cancer Cell* 4:437-450 (2003), which is hereby incorporated by reference in its entirety). At 8 weeks post-implantation, the abundance of CD45$^+$ cells in GFP-Kras$^{G12D}$-PDEC pancreata was similar to that observed in pancreata from 12-week-old p48-Cre LSL-Kras$^{G12D}$ mice (FIG. 2B), which typically display at this stage early PanIN lesions that are scattered throughout the organ (Hingorani et al., "Preinvasive and Invasive Ductal Pancreatic Cancer and its Early Detection in the Mouse," *Cancer Cell* 4:437-450 (2003), which is hereby incorporated by reference in its entirety). By-and-large the distribution of the major immune cell subtypes was similar in both models (FIG. 1C). In addition, both models displayed an increased intrapancreatic as well as splenic accumulation of Gr1$^+$CD11b$^+$ myeloid cells and CD4$^+$Foxp3$^+$CD25$^+$ regulatory T cells (Tregs) as compared with normal pancreas and spleen (FIG. 1D; FIGS. 2C and 2D), in agreement with the reported increase in the abundance of these putative immunosuppressive cell populations during early pancreatic neoplasia (Clark et al., "Dynamics of the Immune Reaction to Pancreatic Cancer From Inception to Invasion," *Cancer Res.* 67:9518-9527 (2007), which is hereby incorporated by reference in its entirety). Together, these observations credential the use of Kras$^{G12D}$-PDEC to elucidate the interaction of the neoplastic epithelium with the host immune system and suggest that oncogenic activation of Kras may be sufficient to instigate immune responses that contribute to disease progression.

Figures 3A, 3B, 3C, 3D:
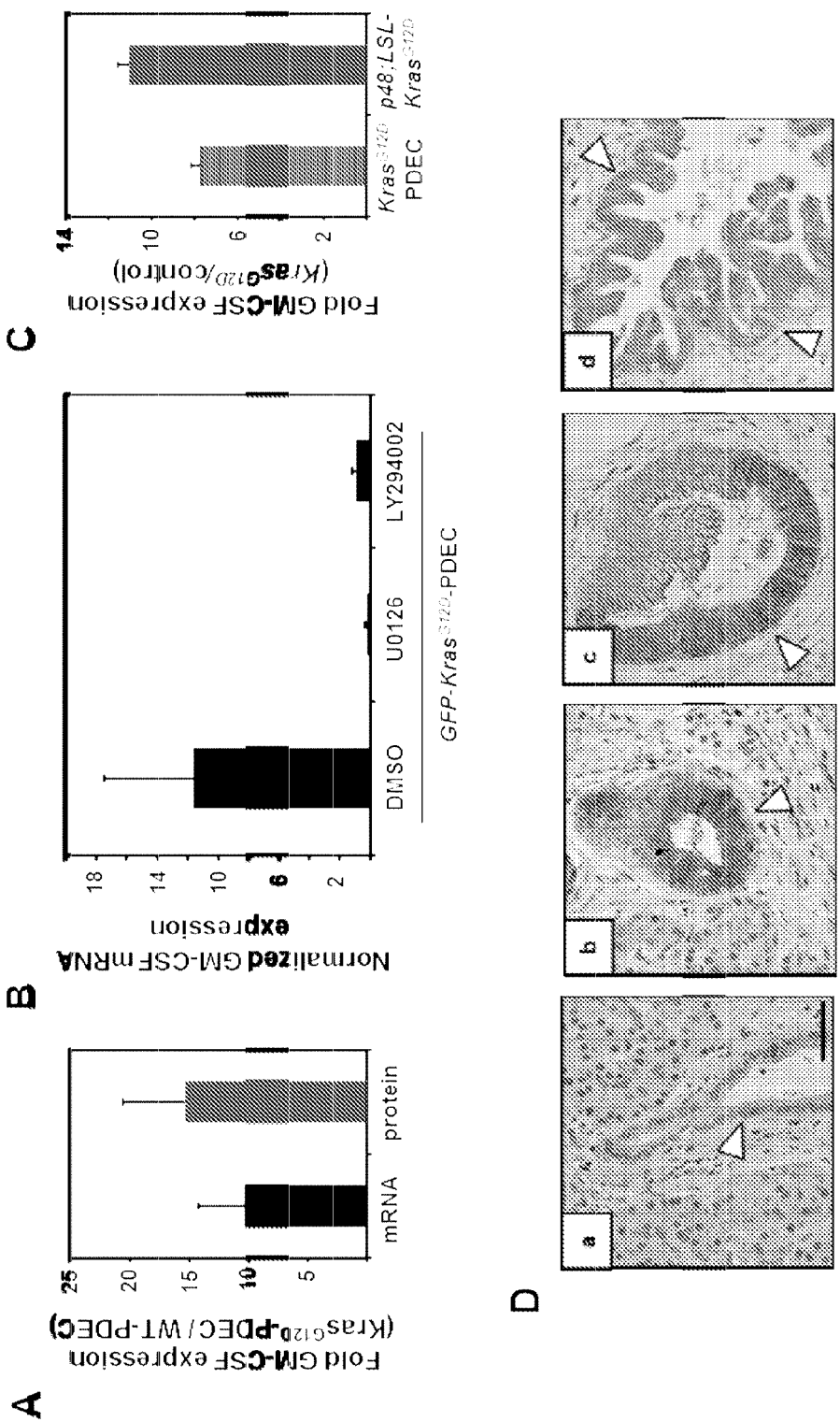
FIGS. 3A-3D shows GM-CSF upregulation in supernatants from Kras$^{G12D}$-PDEC as well as PanIN-harboring mouse and human pancreata.

To further test this idea, the mechanisms by which the expression of oncogenic Kras in PDEC could elicit an immune reaction were identified. Given the documented effect of oncogenic forms of Ras on the expression of immune mediators (Ancrile et al., "Oncogenic Ras-Induced Expression of Cytokines A New Target of Anti-Cancer Therapeutics," *Mol. Interv.* 8:22-27 (2008) and Coppé et al., "Senescence-Associated Secretory Phenotypes Reveal Cell-Nonautonomous Functions of Oncogenic RAS and the P53 Tumor Suppressor," *PLoS Biol.* 6:2853-2868 (2008), which are hereby incorporated by reference in their entirety), the supernatants of wild-type and GFP-Kras$^{G12D}$-PDEC were analyzed for cytokine production using the Milliplex cytokine bead array system (FIG. 3A and FIG. 4A). Of the 32 cytokines represented in this array, GM-CSF was most robustly upregulated in GFP-Kras$^{G12D}$-PDECs (FIG. 3A and FIG. 4A). The increase in GM-CSF protein levels was corroborated by an increase in the levels of GM-CSF transcripts, suggesting a role for Kras$^{G12D}$ in the transcriptional upregulation of GM-CSF (FIG. 3A). Pharmacological inhibition of either PI-3K (LY294002) or MAPK (U0126) pathways resulted in abrogation of GM-CSF expression in Kras$^{G12D}$-PDEC indicating that the regulation of GM-CSF expression by oncogenic Kras is mediated by multiple effector pathways (FIGS. 3B and 4B).

To examine whether increased GM-CSF expression is also a feature of pancreatic neoplasia in vivo, the production of GM-CSF in tissue supernatants from GFP-Kras$^{G12D}$-PDEC and p48-Cre LSL Kras$^{G12D}$ pancreata was measured by ELISA analysis and compared to that from normal pancreatic tissues. In both model systems, GM-CSF levels were found to be significantly upregulated (FIG. 3C). Furthermore, immunohistochemical staining revealed increased GM-CSF in both early and more advanced human PanIN lesions. At least 75% of all PanINs within a section had to exhibit 50% or more GM-CSF-stained cells per lesion to be considered positive. Using this criterion, 14 of the 16 PDA patient samples were positive for GM-CSF staining of PanIN lesions (FIG. 3D). Invasive PDA lesions were also positive for GM-CSF expression, indicating that GM-CSF upregulation persists through disease progression (FIG. 3D).

Of note, compared to PDA-associated PanIN lesions, pancreatic lesions from four non-PDA cases (chronic pancreatitis, pancreatic dermoid cyst, pancreatic endocrine neoplasm, and serous cystadenoma) had no detectable GM-CSF expression (FIG. 4C). Because these diseases typically are not associated with mutations in the Kras allele, the absence of GM-CSF expression is consistent with a role for oncogenic Kras signaling in GM-CSF upregulation. Thus, heightened tumor cell-derived GM-CSF levels may represent an early $Kras^{G12D}$-dependent facet of pancreatic neoplasia that is sustained over the course of malignant.

Figures 5A, 5B, 5C:
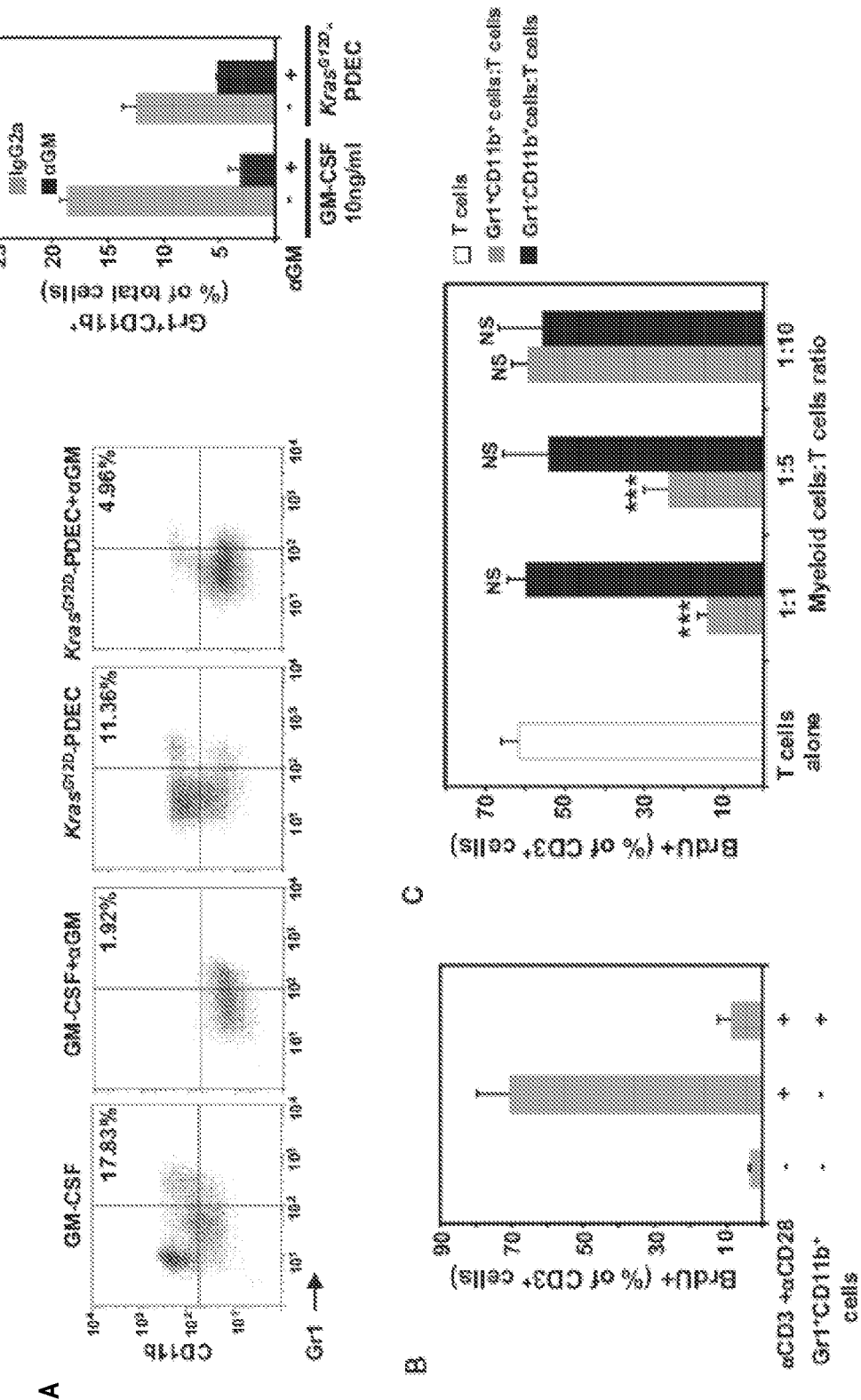
FIGS. 5A-5H show Kras$^{G12D}$-PDECs promote accumulation of immunosuppressive Gr1$^+$CD11b$^+$ cells in a GM-CSF dependent manner.

GM-CSF plays a versatile role in the development of immunological responses and has been implicated in the regulation of proliferation and maturation of multiple immune cell lineages including monocyte, granulocyte, dendritic cells and putative immunosuppressive $Gr1^+CD11b^+$ myeloid cells (Barreda et al., "Regulation of Myeloid Development and Function by Colony Stimulating Factors," *Dev. Comp. Immunol.* 28:509-554 (2004), which is hereby incorporated by reference in its entirety). Because $Gr1^+CD11b^+$ cell accumulation is consistently observed in GFP-$Kras^{G12D}$-PDEC and p48-Cre LSL-$Kras^{G12D}$ pancreata (FIG. 1D), whether the GM-CSF produced by GFP-$Kras^{G12D}$-PDEC could induce the differentiation of progenitor $Gr1^-CD11b^-$ cells to $Gr1^+CD11b^+$ was determined. As illustrated in FIG. 5A, the co-culturing of bone marrow derived $Lin^{neg}CD34^+$ hematopoietic progenitor cells ("HPCs") with GFP-$Kras^{G12D}$-PDECs that were seeded on Transwell inserts, induced the accumulation of $Gr1^+CD11b^+$ cells. Recombinant GM-CSF was used as a positive control (FIG. 5A). The addition of neutralizing anti-GM-CSF monoclonal antibody MP1-22E9 (α-GM) (Schon et al., "Critical Role of Neutrophils for the Generation of Psoriasiform Skin Lesions in Flaky Skin Mice," *J. Invest. Dermatol.* 114:976-983 (2000), which is hereby incorporated by reference in its entirety) significantly attenuated the expansion of $Gr1^+CD11b^+$ cells indicating that their generation is largely dependent on GFP-$Kras^{G12D}$-PDEC-derived GM-CSF (FIG. 5A). To establish whether these $Gr1^+CD11b^+$ cells display suppressive activity, the co-culture derived sorted double positive population was incubated with splenic T cells and the CD3/CD28-induced proliferation of $CD3^+$ T cells was assessed by BrdU incorporation. The proliferation of $CD3^+$ cells was essentially inhibited in the presence of $Gr1^+CD11b^+$ cells indicating that GM-CSF produced by GFP-$Kras^{G12D}$-PDECs can drive the generation of differentiated $Gr1^+CD11b^+$ myeloid cells with immunosuppressive potential (FIG. 5B). Significantly, $Gr1^+CD11b^+$ double-positive cells but not $Gr1^-CD11b^-$ single positive cells isolated from GFP-$Kras^{G12D}$-PDECs grafted pancreata suppressed proliferation of splenic T cells (FIG. 5C), indicating that the accumulation of $Gr1^+CD11b^+$ cells at the sites of pancreatic neoplasia could contribute to the induction of a tolerogenic immune state. Because the numbers of $Gr1^+CD11b^+$ cells were augmented in the spleens of orthotopically injected animals, whether there was a systemic increase in the levels of GM-CSF following engraftment of GFP-$Kras^{G12D}$-PDECs was determined. The levels of circulating GM-CSF in mice with GFP-$Kras^{G12D}$-PDEC lesions were significantly elevated as compared to control animals (FIG. 5D), suggesting that, in addition to its localized intrapancreatic effect, GM-CSF production by GFP-$Kras^{G12D}$-PDECs may affect hematopoietic processes in secondary lymphoid organs.

Figures 5D, 5E, 5F, 5G, 5H:
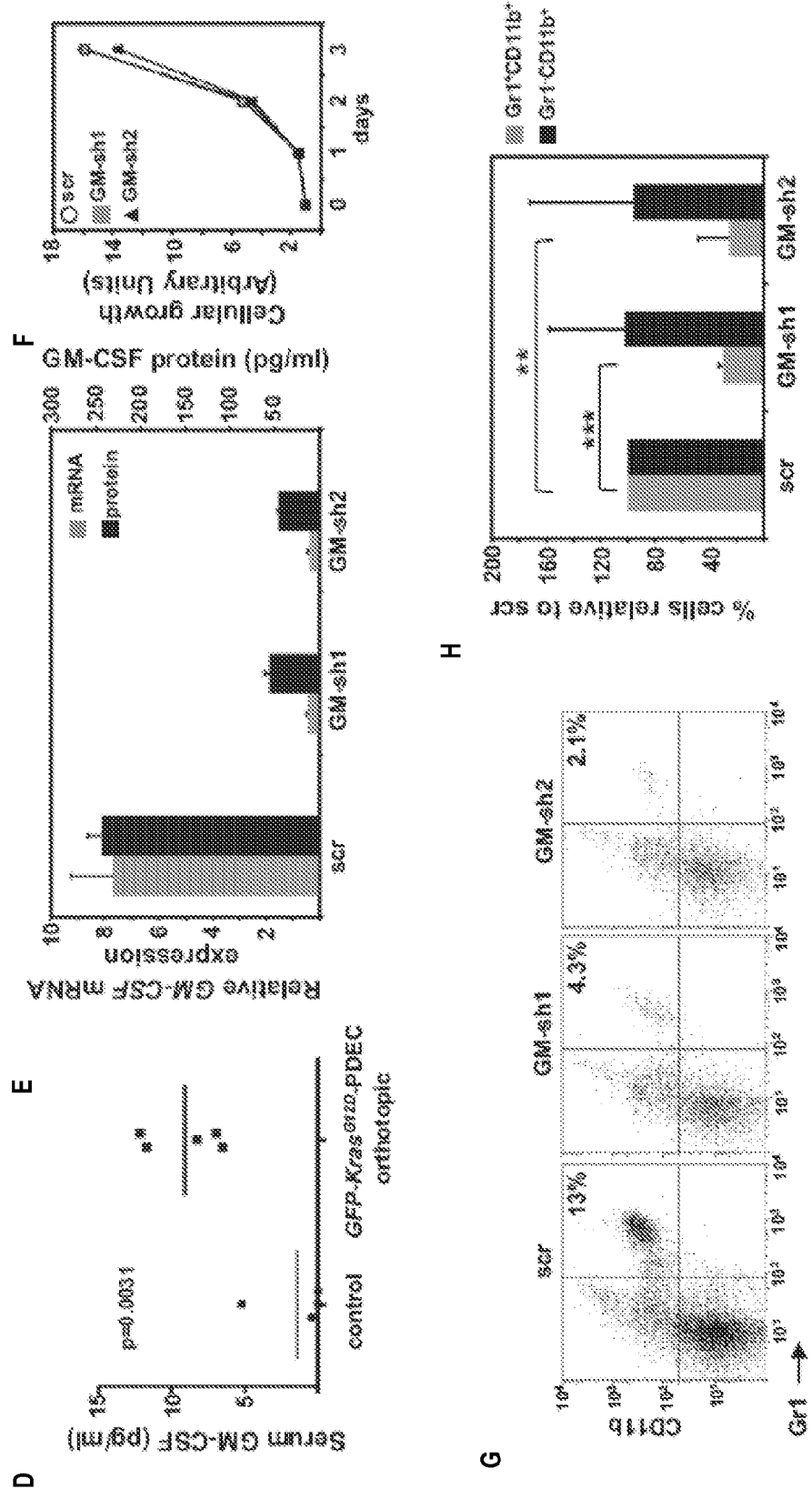

To establish whether the upregulation of GM-CSF in GFP-$Kras^{G12D}$-PDEC can instigate the accumulation of $Gr1^+CD11b^+$ in vivo, a short hairpin RNAi was utilized to stably knock-down GM-CSF expression in GFP-$Kras^{G12D}$-PDECs. A significant reduction of GM-CSF at the level of both mRNA and protein was achieved using two independent hairpin sequences (FIG. 5E). GM-CSF knock-down did not produce an adverse effect on the growth of GFP-$Kras^{G12D}$-PDEC in culture (FIG. 5F), consistent with the findings that these cells do not express the GM-CSF receptor beta chain CD131. The composition of leukocytic infiltrates in pancreata grafted with GFP-$Kras^{G12D}$-PDEC expressing scramble (scr) or GM-CSF shRNAs (GM-sh and GM-sh2) was analyzed. Among all $CD45^+$ cells found in the pancreas, GM-CSF knock-down led to a specific reduction in the abundance of $Gr1^+CD11b^+$ cells but not $Gr1^-CD11b^+$ cells (FIGS. 5G and 5H), indicating that the production of GM-CSF by ductal cells harboring $Kras^{G12D}$ allele is necessary to promote local accumulation of immune cells of the $Gr1^+CD11b^+$ lineage.

Figures 6A, 6B:
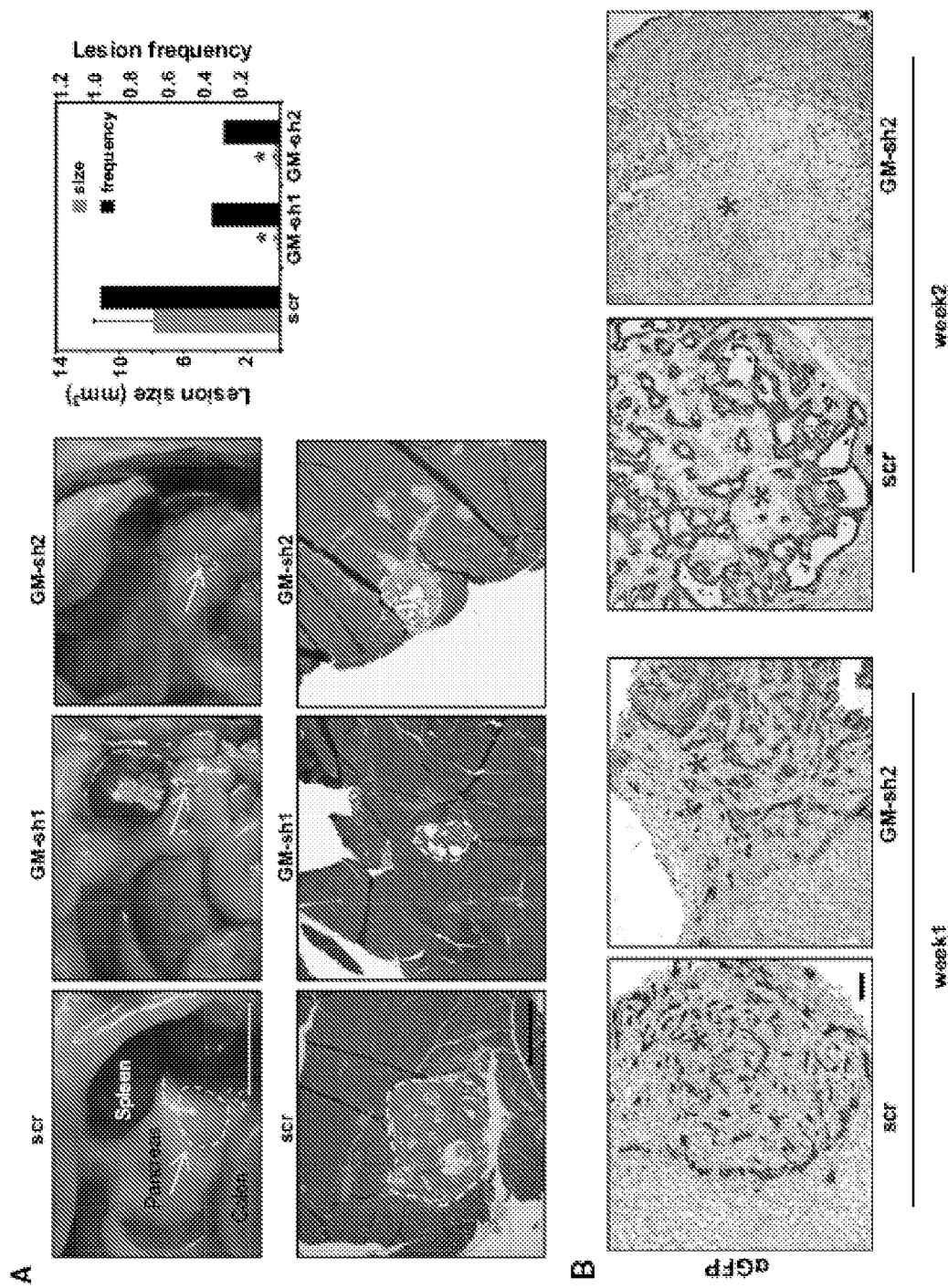
FIGS. 6A-6B depict the functional consequence of ablating GM-CSF on growth of Kras$^{G12D}$-PDEC in vivo. The top three photomicrographs of FIG. 6A provide a gross anatomical view of scr and GM-sh Kras$^{G12D}$-PDEC grafts (dotted outlines and arrows) at 8 weeks post-implantation. Scale bars=5 mm. Quantification of the graft size at 8 weeks post-implantation (gray bars, left axis) and percentage of overall lesion frequency (black bars, right axis) is indicated in the graph of FIG. 6A. Error bars indicate SD (n=3). Sections from pancreata containing scr- and GM-sh GFP-Kras$^{G12D}$-PDEC orthotopic grafts at 4 weeks post-implantation were stained with H&E (FIG. 6A, bottom three images). Lesions are delineated by dotted lines. Scale=500 µm.
Figure 7:
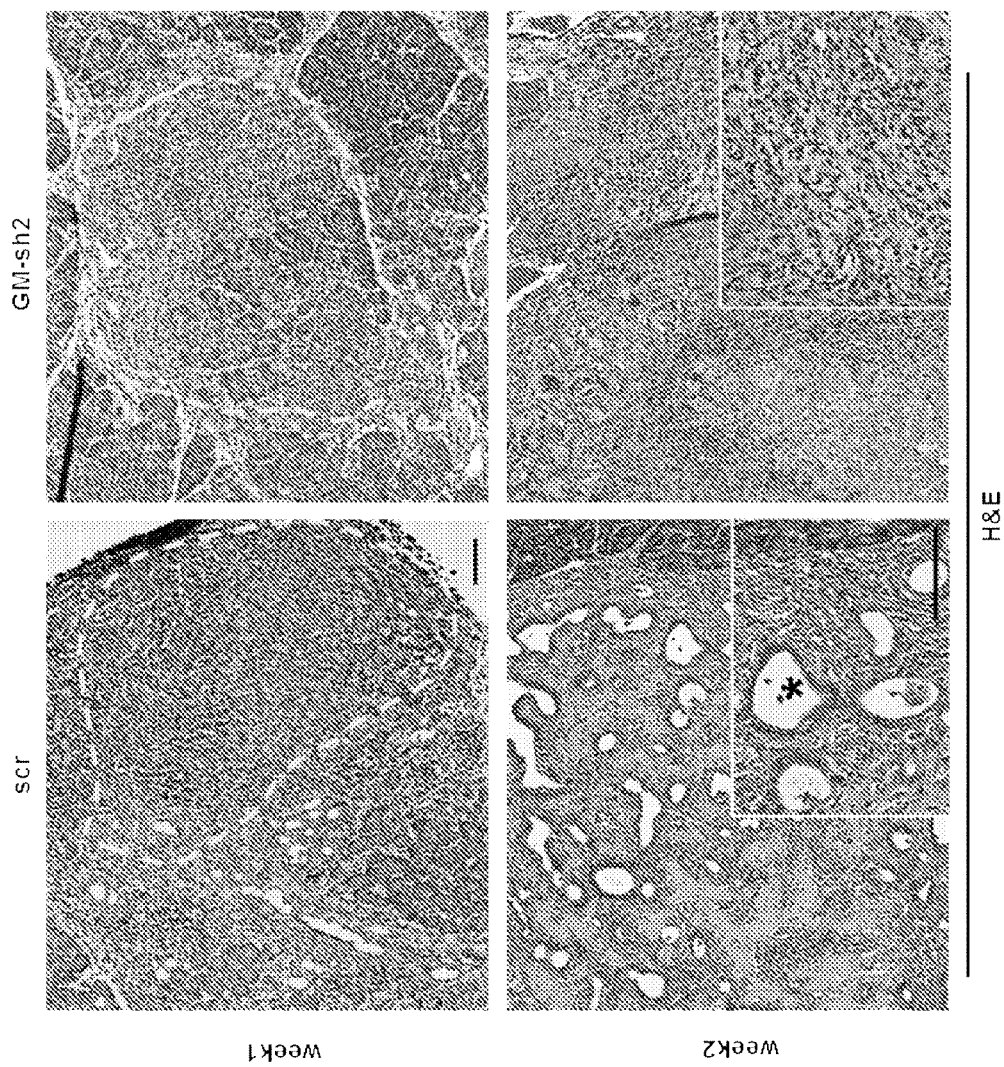
FIG. 7 are phase contrast images showing H&E staining of the lesions formed by scr- and GM-sh GFP-Kras$^{G12D}$-PDEC at 1 week (top images; dotted outline) and 2 weeks (bottom images) post-implantation. Insets show magnified areas of images from week 2 time-point. Asterisk indicates pancreatic neoplastic duct. Scale bars=100 µm. n=6 mice per group.

As $Gr1^+CD11b^+$ myeloid cells have been implicated in tumor-induced immune tolerance (Gabrilovich and Nagaraj et al., "Myeloid-Derived Suppressor Cells As Regulators of the Immune System," *Nature Rev. Immunol.* 9:162-179 (2009), which is hereby incorporated by reference in its entirety), it was reasoned that the $Kras^{G12D}$-PDEC-mediated production of GM-CSF and the resulting accumulation of $Gr1^+CD11b^+$ cells could be critical for the establishment of an immunosuppressive environment that is growth permissive. To investigate this possibility, the engraftment of GFP-$Kras^{G12D}$-PDEC was characterized in relation to GM-CSF production. As illustrated in FIG. 6A the implantation frequency of GM-sh GFP-$Kras^{G12D}$-PDECs was significantly reduced as compared to control scr GFP-$Kras^{G12D}$-PDECs, and the average size of the knock-down lesions was significantly decreased. To gain insight into the process underlying compromised engraftment of GM-sh GFP-$Kras^{G12D}$-PDECs, the fate of the grafts at different time points post-implantation was analyzed by immunohistochemical staining of GFP-labeled $Kras^{G12D}$-PDEC. At one week post implantation, grafts generated from scr- and GM-sh GFP-$Kras^{G12D}$-PDECs were essentially indistinguishable with respect to size, histological appearance, and cell number (FIG. 6B and FIG. 7). Thus it appears that GM-CSF deficiency has no adverse effect on the initial growth and survival capabilities of $Kras^{G12D}$-PDEC in vivo. However, at two weeks post-implantation, while scr GFP-$Kras^{G12D}$-PDEC grafts displayed a sizable expansion and the characteristic elaboration of ductal structures, graft areas in pancreata that were implanted with GM-sh GFP-$Kras^{G12D}$-PDECs were virtually devoid of GFP positive cells (FIG. 6B and FIG. 7). These observations are consistent with the postulate that the production of GM-CSF enables $Kras^{G12D}$-PDEC to engage host-dependent responses that favor their maintenance and expansion.

Figures 8A, 8B:
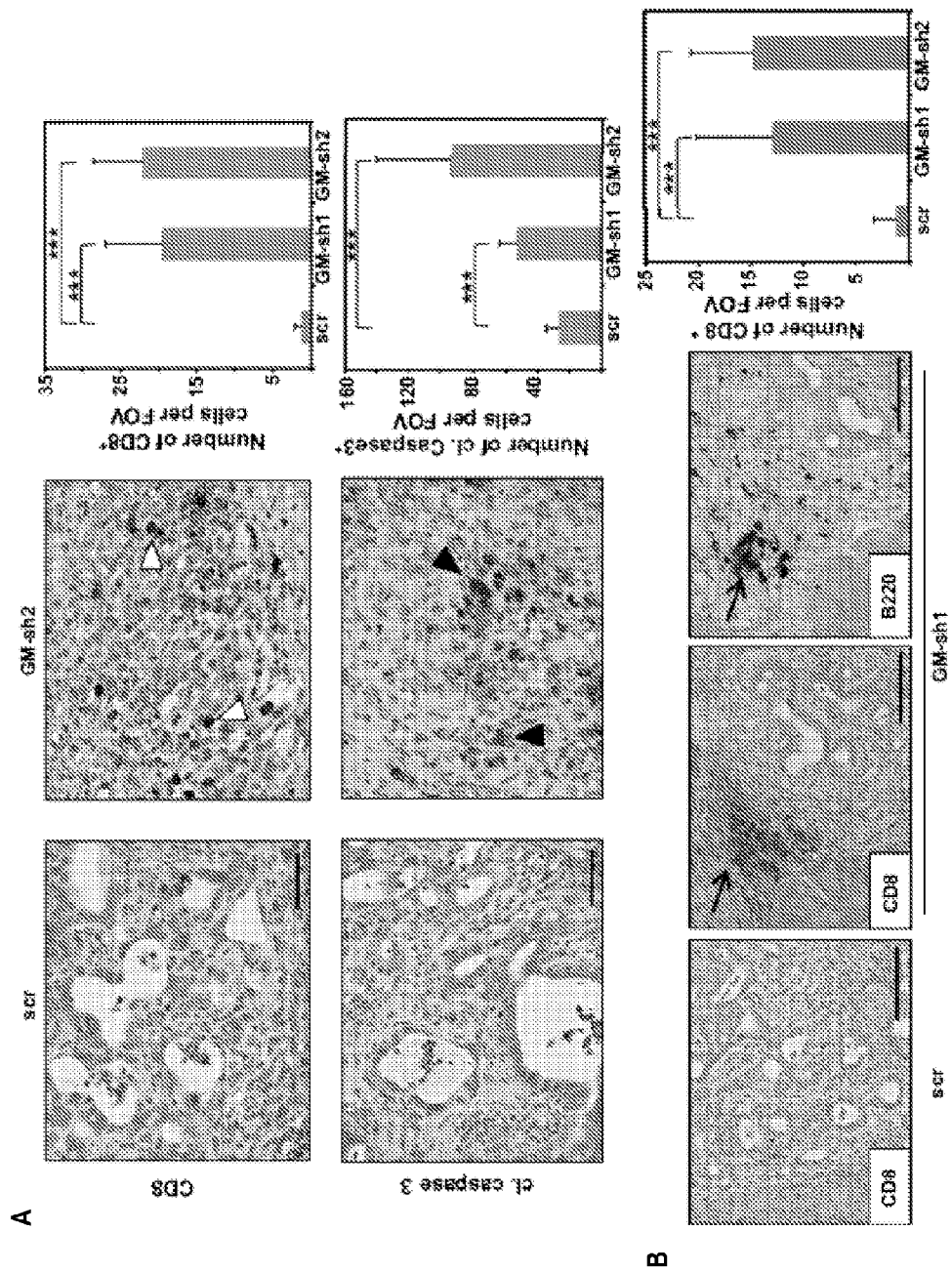
FIGS. 8A-8B demonstrate that engraftment of GM-CSF knock-down Kras$^{G12D}$-PDEC is accompanied by an increase in infiltrating CD8$^+$ T cells.
Figure 9A:
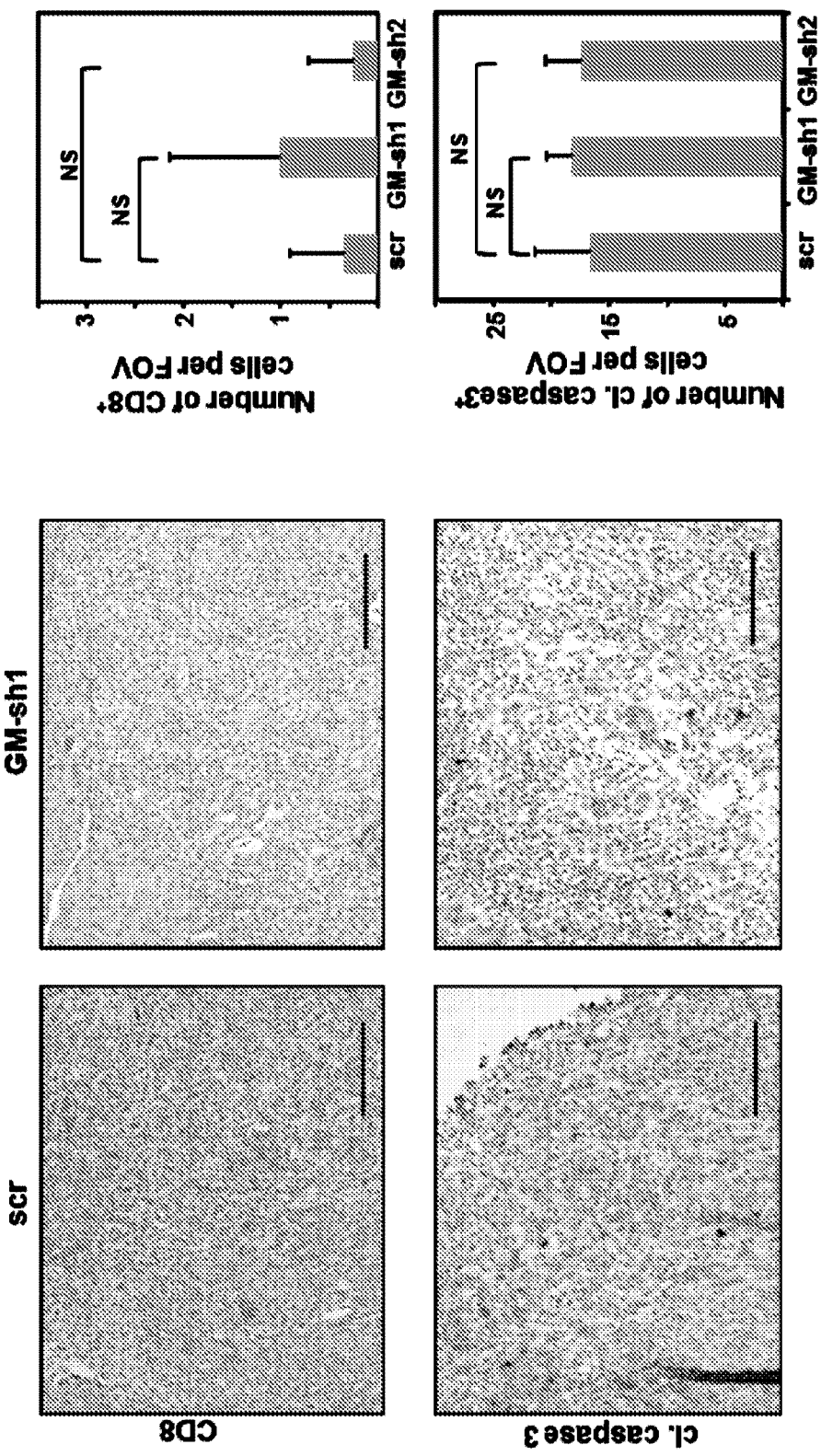
FIGS. 9A-9B show infiltration of CD8+ T cells upon engraftment of GM-CSF knock-down Kras$^{G12D}$-PDEC.
Figure 9B:
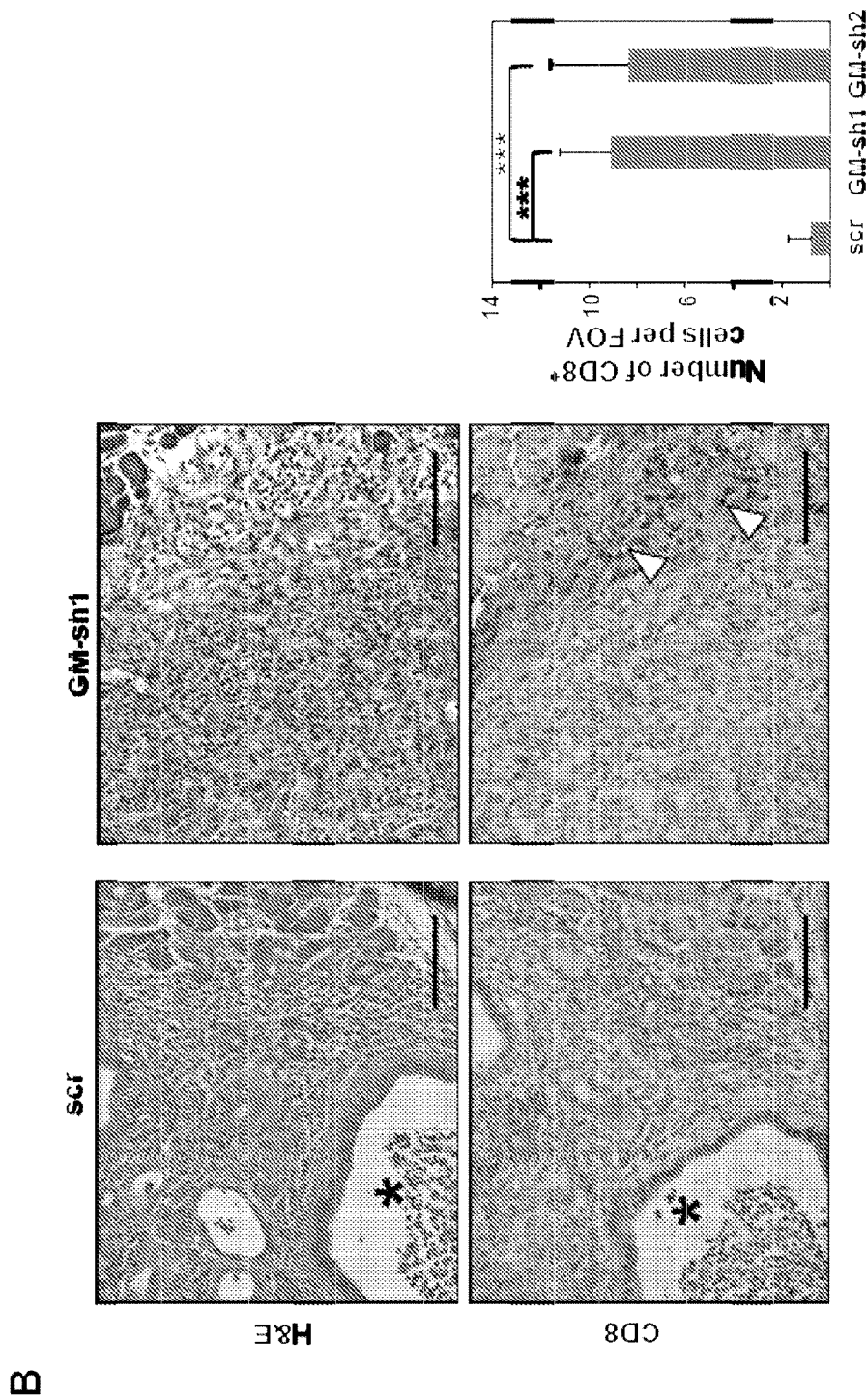

Recent studies have indicated that $Gr1^+CD11b^+$ cells may contribute to tumor immune evasion by restraining the activity of $CD8^+$ T cells (Gabrilovich and Nagaraj et al., "Myeloid-Derived Suppressor Cells As Regulators of the Immune System," *Nature Rev. Immunol.* 9:162-179 (2009), which is hereby incorporated by reference in its entirety). To examine the relevance of this mechanism to the engraftment potential of $Kras^{G12D}$-PDECs, the accumulation of $CD8^+$ T cells was analyzed by immunohistochemistry. The pancreatic parenchyma associated with grafts from scr GFP-$Kras^{G12D}$-PDEC was devoid of $CD8^+$ T cells both at one and two weeks post implantation (FIGS. 8A and 9A). In contrast, a pronounced accumulation of $CD8^+$ T cells in the parenchyma of GM-sh GFP-$Kras^{G12D}$-PDEC grafts was detected at 2 weeks post implantation (FIG. 8A). Significantly no infiltration of CD8+ cells was observed at 1 week post-implantation in GM-sh-GFP-Kras$^{G12D}$-PDEC grafts (FIG. 9A) consistent with the time requirement associated with the priming of the adaptive immune responses. Of note, at later time points post-implantation (~4 weeks) some of the CD8+ T cells were found in clusters that contain B cells, likely signifying the formation of secondary lymphoid tissue, which is indicative of a persistent immune response (FIG. 8B; Carragher et al., "Ectopic Lymphoid Tissues and Local Immunity," Semin. Immun. 20: 26-42 (2008), which is hereby incorporated by reference in its entirety).

Figures 10A, 10B, 10C:
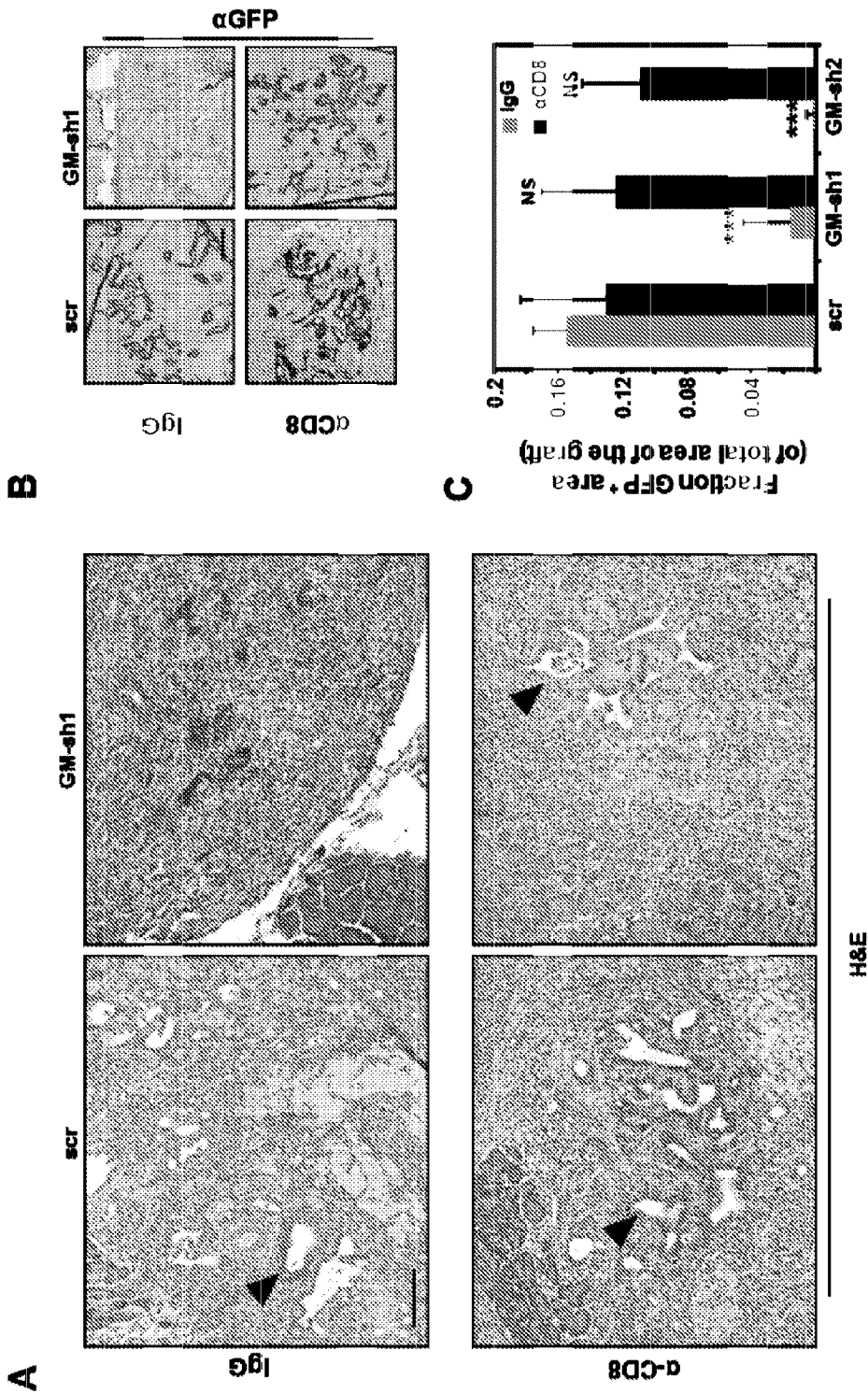
FIGS. 10A-10C show that CD8+ T cells are instrumental in the clearance of GM-CSF knock-down of Kras$^{G12D}$-PDECs. Orthotopic grafts formed by scr- or GM-sh GFP-Kras$^{G12D}$-PDECs implanted into either mock-depleted (IgG) or CD8-depleted animals were analyzed at 2 weeks after implantation by H&E staining as shown in FIG. 10A. Black arrowheads indicate pancreatic ductal structures. Scale bar, 100 mm.
Figure 11:
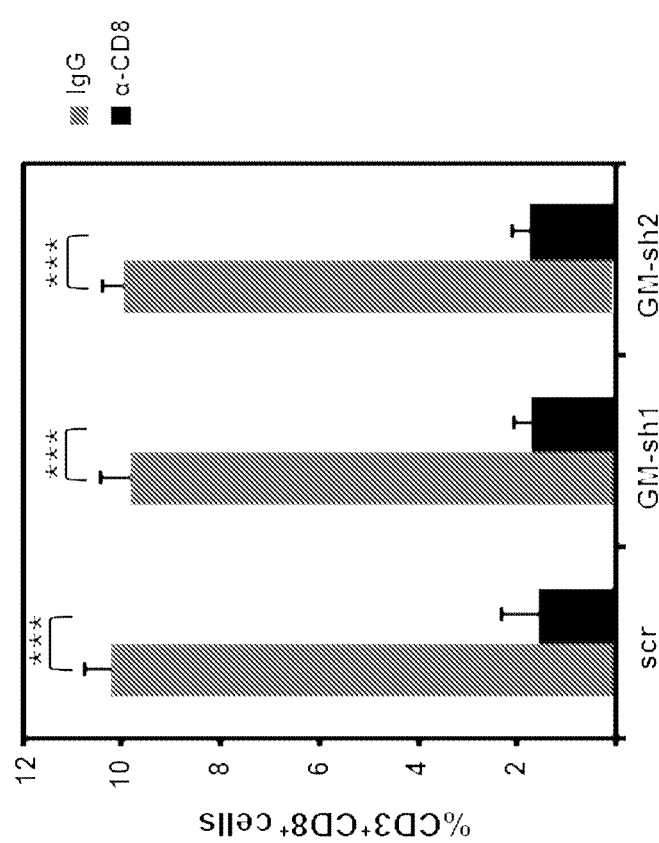
FIG. 11 is a graph of CD8$^+$ T cell-depletion in the mouse spleens as assessed by flow cytometric analysis. CD8$^+$ T cells were depleted by intraperitoneal injections of anti-CD8 antibody. Isotype control antibody was used as a mock-depletion control. Error bars indicate SD, (n=3 mice per group). p value: ***<0.001

Coincident with the accumulation of CD8+ T cells, an increase in the frequency of apoptosis within the GM-CSF knock-down grafts was observed only two weeks after implantation (FIGS. 8A and 9A). These results suggest that, in the absence of GM-CSF, the cytotoxic activity of CD8+ T cells at the site of engraftment may be responsible for the clearance of implanted GFP-Kras$^{G12D}$-PDEC. A prediction borne by this interpretation is that the growth defect of GM-sh Kras$^{G12D}$-PDEC would be rescued by CD8+ T cell depletion. To test this prediction, orthotopic implantations were performed in animals depleted of CD8+ T cells by intraperitoneal administration of anti-CD8 antibody over a period of two weeks. This regimen resulted in >90% depletion of CD3+CD8+ T cells (FIG. 11). At 2 weeks post-implantation animals injected with control antibody contained virtually no GM-sh GFP-Kras$^{G12D}$-PDEC (FIGS. 10A-10C) and maintained high apoptotic rates. In contrast, the injection of anti-CD8 antibody was sufficient to permit the establishment of GM-sh GFP-Kras$^{G12D}$-PDEC grafts that were indistinguishable in size and overall appearance from scr GFP-Kras$^{G12D}$-PDEC grafts (FIGS. 10A-10C), indicating that CD8+ T cells are the primary immune cell type responsible for mounting and executing the immune response against Kras$^{G12D}$-PDEC.

The critical role of host immunity in regulating tumorigenesis is undisputed. Furthermore, it is becoming increasingly evident that immune cells in the tumor microenvironment fail to mount an effective anti-tumor immune response. However, the underlying mechanisms that allow tumors to escape immune surveillance have not been fully characterized. As described herein, oncogenic Kras is involved in restraining the anti-tumor immune response through the production of GM-CSF and the subsequent suppression of T-cell immunity. This immune evasion strategy may contribute to immunotherapeutic resistance in oncogenic Kras driven cancers.

Oncogenic activation of Kras is the earliest and nearly universal genetic lesion detected in pancreatic ductal adenocarcinoma (PDA) and therefore has been postulated to play an instructive role in the initiation and development of this malignancy. In support of this postulate, endogenous expression of activated Kras allele in the mouse pancreas is sufficient to initiate the ordered acquisition of the histopathological changes that are characteristic of the evolution of the disease in humans (Hingorani et al., "Preinvasive and Invasive Ductal Pancreatic Cancer and its Early Detection in the Mouse," Cancer Cell 4:437-450 (2003) and Maitra et al., "Pancreatic Cancer," Annu. Rev. Pathol. 3:157-188 (2008), which are hereby incorporated by reference in their entirety). The progression of pancreatic neoplasia is accompanied by cellular and molecular alterations in both the parenchymal and stromal compartments of the pancreas. The parenchymal component gives rise to precursor lesion termed pancreatic intraepithelial neoplasia (PanIN), and the contribution of oncogenic Kras to this transition has been amply documented using genetically engineered mouse models (Hingorani et al., "Preinvasive and Invasive Ductal Pancreatic Cancer and its Early Detection in the Mouse," Cancer Cell 4:437-450 (2003) and Hingorani et al., "Trp53R172H And Kras$^{g12d}$ Cooperate to Promote Chromosomal Instability and Widely Metastatic Pancreatic Ductal Adenocarcinoma in Mice," Cancer Cell 7:469-483 (2005), which are hereby incorporated by reference in their entirety). In contrast, little is known about the stroma-modulating capabilities of oncogenic Kras during the early stages of pancreatic cancer. The demonstration that GM-CSF production in response to activation of Kras modulates the immune reaction to pancreatic precursor lesion thus provides new insights into how this oncogenic event could lead to the reprogramming of the microenvironment from the very beginning of the disease. The recent demonstration of the role of pancreas-specific oncogenic activation of Kras in generating a pro-tumorigenic inflammatory microenvironment (Fukuda et al., "Stat3 and MMPI Contribute to Pancreatic Ductal Adenocarcinoma Initiation and Progression," Cancer Cell 19:441-455 (2011) and Lesina et al., "Stat3/Socs3 Activation by IL-6 Transsignaling Promotes Progression of Pancreatic Intraepithelial Neoplasia and Development of Pancreatic Cancer," Cancer Cell 19:456-469 (2011), which are hereby incorporated by reference in their entirety), further underscores the crucial contribution of non-cell autonomous mechanisms to pancreatic tumor initiation and progression.

The identification of GM-CSF as a transcriptional target of oncogenic Kras in PDEC is consistent with the existence of Ras-regulated transcription factor binding sites, such as AP-1 and ETS, in the GM-CSF promoter region (Osborne et al., "Transcriptional Regulation of Mouse Granulocyte-Macrophage Colony-Stimulating Factor/IL-3 Locus," J. Immunol. 155:226-235 (1995), which is hereby incorporated by reference in its entirety). The patho-physiological relevance of the activation of this transcriptional program is indicated by the increased levels of GM-CSF that were observed in human PanIN lesions. It is possible that a similar Kras-mediated mechanism of GM-CSF regulation is responsible for the enhanced serum levels of GM-CSF detected in patients with pancreatic cancer (Mroczko et al., "Hematopoietic Cytokines in the Sera of Patients with Pancreatic Cancer," Clin. Chem. Lab. Med. 43(2):146-150 (2005), which is hereby incorporated by reference in its entirety). The initial analysis described herein suggests that the upregulation of GM-CSF in response to oncogenic Kras is mediated by the concerted action of multiple effector pathways including the Erk and PI-3K (FIG. 3B). As these pathways are frequently activated in various malignancies, the induction of GM-CSF is not likely restricted to oncogenic Kras driven cancers and/or the pancreas. This idea is supported by studies demonstrating the overexpression of GM-CSF in several human cancer lines including those of breast, bladder and melanoma origin (Bronte et al., "Unopposed Production of Granulocyte-Macrophage Colony-Stimulating Factor by Tumors Inhibits CD8+ T Cell Responses by Dysregulating Antigen-Presenting Cell Maturation," J. Immunol. 162:5728-5737 (1999); Dolcetti et al., "Hierarchy of Immunosuppressive Strength Among Myeloid-Derived Suppressor Cell Subsets is Determined By GM-CSF," Eur. J. Immunol. 40:22-35 (2010); and Steube et al., "Secretion of Functional Hematopoietic Growth Factors by Human Carcinoma Cell Lines," Int. J. Cancer 78:120-124 (1998), which are hereby incorporated by reference in their entirety). Thus the functional significance GM-CSF upregulation has broader implications.

Under normal physiological conditions, GM-CSF serves as a bona fide growth factor for hematopoietic cells promoting the proliferation and maturation of multiple myeloid cell lineages in a concentration dependent manner (Barreda et al., "Regulation of Myeloid Development and Function by Colony Stimulating Factors," *Dev. Comp. Immunol.* 28:509-554 (2004), which is hereby incorporated by reference in its entirety). In neoplastic settings, GM-CSF has been shown to be endowed with the potential to exert both pro and anti-tumorigenic effects by suppressing or enhancing tumor immunity, respectively. The findings described herein demonstrate that, in pancreatic ductal cells harboring oncogenic Kras, GM-CSF production is linked to the expansion of $Gr1^+CD11b^+$ myeloid cells. A similar consequential relationship between GM-CSF generation and $Gr1^+CD11b^+$ cell expansion has been documented in other tumor models (Dolcetti et al., "Hierarchy of Immunosuppressive Strength Among Myeloid-Derived Suppressor Cell Subsets is Determined By GM-CSF," *Eur. J. Immunol.* 40:22-35 (2010); Marigo et al., "Tumor-Induced Tolerance and Immune Suppression Depend on the C/Ebpbeta Transcription Factor," *Immunity* 32:790-802 (2010); Morales et al., "GM-CSF is One of the Main Breast Tumor-Derived Soluble Factors Involved in the Differentiation of $CD11b^-Gr1^-$ Bone Marrow Progenitor Cells Into Myeloid-Derived Suppressor Cells," *Breast Cancer Res. Treat.* 123:39-49 (2010)). However, in the mouse, $Gr1^+CD11b^+$ double positive cells represent a heterogeneous population comprised of myeloid derived suppressor cells, monocytes and immature myeloid cells (Ostrand-Rosenberg et al., "Myeloid-Derived Suppressor Cells: Linking Inflammation and Cancer," *J. Immunol.* 182:4499-4506. (2009), which is hereby incorporated by reference in its entirety). Both the in vitro and in vivo studies described herein point to the immunosuppressive nature of the $Gr1^+CD11b^+$ cells that accumulate in response to GM-CSF production by pancreatic precursor lesions. First, when isolated from pancreata grafted with $GFP-Kras^{G12D}$-PDECs, the $Gr1^+CD11b^+$ cells displayed a suppressive effect in a T cell proliferation assay. Second, the reduction in the abundance of $Gr1^+CD11b^+$ cells following the suppression of GM-CSF expression in vivo was accompanied by the infiltration of $CD8^+$ T cells. Third, the immune response-mediated elimination of orthotopic $GFP-Kras^{G12D}$-PDECs lesions observed under these conditions could be fully rescued by $CD8^+$ T cell depletion, indicating a principal role for $Gr1^+CD11b^+$ cells in disrupting T cell immune surveillance during the early stages of pancreatic neoplasia. The potential relevance of this immune modulatory mechanism to more advanced stages of pancreatic cancer is suggested by the reciprocal relationship between $CD8^+$ T and $Gr1^+CD11b^+$ cell infiltrates observed in pancreatic tumors from the LSL-$Kras^{G12D}$ mice (Clark et al., "Dynamics of the Immune Reaction to Pancreatic Cancer From Inception to Invasion," *Cancer Res.* 67:9518-9527 (2007), which is hereby incorporated by reference in its entirety).

GM-CSF is not unique in its ability to promote the expansion and tumor mobilization of $Gr1^+CD11b^+$ immunosuppressive cells. For example, IL1-β, IL-6 and VEGF have been shown to induce the accumulation of $Gr1^+CD11b^+$ myeloid cells and the concomitant suppression T cell immune response in a variety of mouse tumor models (Bunt et al., "Reduced Inflammation in the Tumor Microenvironment Delays the Accumulation of Myeloid-Derived Suppressor Cells and Limits Tumor Progression," *Cancer Res.* 67:10019-10026 (2007); Melani et al., "Myeloid Cell Expansion Elicited by the Progression of Spontaneous Mammary Carcinomas in C-Erbb-2 Transgenic BALB/C Mice Suppresses Immune Reactivity," *Blood* 102:2138-2145 (2003); and Tu et al., "Overexpression of Interleukin-1beta Induces Gastric Inflammation and Cancer and Mobilizes Myeloid-Derived Suppressor Cells In Mice," *Cancer Cell* 14:408-419 (2008), which are hereby incorporated by reference in their entirety). Significantly, IL1-β, IL-6 and VEGF are targets of oncogenic Ras signaling and their production by cancer cells harboring oncogenic Ras has been implicated in various pro-tumorigenic processes such as inflammation, angiogenesis and metastasis. Since the expression of IL1-β, IL-6 and VEGF in $GFP-Kras^{G12D}$-PDECs is not elevated relative to the levels measured in wild-type PDEC (FIG. 4A), the production of GM-CSF by the precursor lesions formed by these cells form is necessary and sufficient to induce the observed increase in $Gr1^+CD11b^+$ cells and the impaired response of $CD8^+$ T cells. The molecular mechanisms responsible for the selective upregulation of GM-CSF observed in $GFP-Kras^{G12D}$-PDECs remain to be defined. Differences in genetic profile, cellular background, and levels of Ras expression between the experimental system described herein and those used in other reports could be important contributors. However, it remains formally possible that IL1-β, IL-6 and VEGF as well as potentially other secreted factors can participate in establishing an immunosuppressive environment in oncogenic Ras-driven cancers. The existence of such redundancy in the mechanism by which oncogenic Ras can invoke tumor-induced tolerance may serve to secure the sustenance of this mechanism at various stages of tumor development.

The studies described herein reinforce the role of intrinsic immune surveillance in restraining tumor initiation and support the idea that the evolution of pancreatic neoplasia is critically dependent on the subversion of T cell responses against antigens that are expressed by pancreatic tumor cells. Although the specific antigen recognized by the $CD8^+$ cells in this experimental system remains to be identified, it is of relevance to note that a T cell response against oncogenic Ras has been documented in a significant proportion of patients with PDA (Gedde-Dahl et al., "T Cell Epitopes Encompassing the Mutational Hot Spot Position 61 of p21 Ras. Promiscuity in Ras Peptide Binding to HLA," *Eur. J. Immunol.* 24:410-414 (1994); Kubuschok et al., "Naturally Occurring T-Cell Response Against Mutated P21 Ras Oncoprotein in Pancreatic Cancer," *Clin. Cancer Res.* 12:1365-1372 (2006); Linard et al., "A Ras-Mutated Peptide Targeted by CTL Infiltrating a Human Melanoma Lesion," *J. Immunol.* 168:4802-4808 (2002); and Weijzen et al., "Modulation of The Immune Response and Tumor Growth by Activated Ras," *Leukemia* 13:502-513 (1999), which are hereby incorporated by reference in their entirety). Given the ubiquitous occurrence of oncogenic Kras mutations in pancreatic adenocarcinomas, the disruption of mechanisms that induce T cell tolerance might offer a broadly applicable strategy for the targeting of immune escape in pancreatic cancer.

Although the invention has been described in detail for the purpose of illustration, it is understood that such detail is solely for that purpose, and variations can be made therein by those skilled in the art without departing from the spirit and scope of the invention which is defined in the following claims.

What is claimed:

1. A method of enhancing anti-tumor immunity in a subject having pancreatic cancer comprising:
   selecting a subject having a pancreatic tumor, wherein the pancreatic tumor cells comprise an activated ras oncogene; and
   administering to the selected subject an agent that inhibits GM-CSF in an amount effective to decrease myeloid derived suppressor cell immunosuppression in the subject, thereby enhancing anti-tumor immunity in the subject.

2. The method of claim 1, wherein the activated oncogene is KRas.

3. The method of claim 1, wherein the agent is an antibody or binding fragment thereof that recognizes GM-CSF.

4. The method of claim 3, wherein the antibody comprises MOR103.

5. The method of claim 1, wherein said administering is carried out in combination with one or more additional cancer related therapies or therapeutics.

6. The method of claim 1, wherein the agent that inhibits GM-CSF is administered directly to the tumor site.

7. The method of claim 1, wherein the agent that inhibits GM-CSF is coupled to a tumor cell targeting ligand to target delivery of the agent to said tumor cells.

* * * * *

UNITED STATES PATENT AND TRADEMARK OFFICE
CERTIFICATE OF CORRECTION

PATENT NO. : 9,901,079 B2
APPLICATION NO. : 14/239503
DATED : February 27, 2018
INVENTOR(S) : Bar-Sagi et al.

Page 1 of 1

It is certified that error appears in the above-identified patent and that said Letters Patent is hereby corrected as shown below:

In the Specification

Column 1 at Lines 11-14, delete "This invention was made with government support under grant number CA055360 awarded by the National Institutes of Health. The government has certain rights in this invention." and insert --This invention was made with government support under CA055360 awarded by National Institutes of Health. The government has certain rights in the invention.--

Signed and Sealed this
Eleventh Day of December, 2018

Andrei Iancu
*Director of the United States Patent and Trademark Office*

SEQUENCE LISTING

<160> NUMBER OF SEQ ID NOS: 3

<210> SEQ ID NO 1
<211> LENGTH: 781
<212> TYPE: DNA
<213> ORGANISM: Homo sapiens

<400> SEQUENCE: 1

```
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat gaatgaaaca gtagaagtca tctcagaaat gtttgacctc caggagccga     240
cctgcctaca gacccgcctg gagctgtaca agcagggcct gcggggcagc ctcaccaagc     300
tcaagggccc cttgaccatg atggccagca ctacaagca gcactgccct ccaaccccgg      360
aaacttcctg tgcaacccag attatcacct ttgaaagttt caaagagaac ctgaaggact     420
ttctgcttgt catccccttt gactgctggg agccagtcca ggagtgagac cggccagatg     480
aggctggcca agccggggag ctgctctctc atgaaacaag agctagaaac tcaggatggt     540
catcttggag ggaccaaggg gtgggccaca gccatggtgg gagtggcctg acctgccct      600 gggccacact gaccctgata caggcatggc agaagaatgg gaatatttta tactgacaga     660
aatcagtaat atttatatat ttatattttt aaaatattta tttatttatt tatttaagtt     720
catattccat atttattcaa gatgttttac cgtaataatt attattaaaa atatgcttct     780
a                                                                     781
```

<210> SEQ ID NO 2
<211> LENGTH: 144
<212> TYPE: PRT
<213> ORGANISM: Homo sapiens

<400> SEQUENCE: 2

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140
```

<210> SEQ ID NO 3
<211> LENGTH: 188
<212> TYPE: PRT
<213> ORGANISM: Mus musculus

```
<400> SEQUENCE: 3

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Glu Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Arg Thr Arg Cys Thr Val Met
                180                 185
```